(12) United States Patent
Ghanbari et al.

(10) Patent No.: US 11,826,421 B2
(45) Date of Patent: Nov. 28, 2023

(54) BACTERIOPHAGE-BASED VACCINES AND ENGINEERED BACTERIOPHAGE

(71) Applicant: Athanor Biosciences, Inc., Halethorpe, MD (US)

(72) Inventors: Hossein A Ghanbari, Potomac, MD (US); Michael S. Lebowitz, Pikesville, MD (US)

(73) Assignee: Athanor Biosciences, Inc., Halethorpe, MD (US)

( * ) Notice: Subject to any disclaimer, the term of this patent is extended or adjusted under 35 U.S.C. 154(b) by 335 days.

(21) Appl. No.: 17/205,671

(22) Filed: Mar. 18, 2021

(65) Prior Publication Data

US 2021/0290760 A1  Sep. 23, 2021

Related U.S. Application Data

(60) Provisional application No. 63/073,908, filed on Sep. 2, 2020, provisional application No. 62/992,394, filed on Mar. 20, 2020.

(51) Int. Cl.

| | |
|---|---|
| *C12N 15/11* | (2006.01) |
| *C12N 7/00* | (2006.01) |
| *C12N 7/01* | (2006.01) |
| *A61K 35/76* | (2015.01) |
| *A61K 39/215* | (2006.01) |
| *A61K 39/295* | (2006.01) |
| *C07K 14/005* | (2006.01) |
| *C12N 15/87* | (2006.01) |
| *A61K 39/00* | (2006.01) |

(52) U.S. Cl.
CPC .......... *A61K 39/295* (2013.01); *C07K 14/005* (2013.01); *C12N 7/00* (2013.01); *C12N 15/87* (2013.01); *A61K 2039/70* (2013.01); *C12N 2795/00034* (2013.01)

(58) Field of Classification Search
CPC .............. C07K 14/005; C07K 2319/00; C12N 2795/10321; C12N 7/00; A61K 39/215
See application file for complete search history.

(56) References Cited

U.S. PATENT DOCUMENTS

| | | |
|---|---|---|
| 8,685,694 B2 | 4/2014 | Rao |
| 9,328,149 B2 | 5/2016 | Rao et al. |
| 2005/0226892 A1 | 10/2005 | Rao |
| 2006/0240456 A1 | 10/2006 | Chen et al. |
| 2021/0309973 A1 | 10/2021 | Ghanbari et al. |

FOREIGN PATENT DOCUMENTS

| | | |
|---|---|---|
| WO | WO 2005/058006 | 6/2005 |
| WO | WO 2008/109398 | 9/2008 |
| WO | WO 2018/050871 | 3/2018 |

OTHER PUBLICATIONS

Ahmed, et al. "Preliminary Identification of Potential Vaccine Targets for the COVID-19 Coronavirus (SARS-COV-2) Based on SARS-COV Immunological Studies" *Viruses* 12:254 (2020) pp. 1-15.
Malik, et al. "Simultaneous display of different peptides on the surface of filamentous bacteriophages" *Nucl. Acids Res.* 25 (1997) pp. 915-916.
Pavoni, et al. "Simultaneous display of two large proteins on the head and tail of bacteriophage lambda" *BMC Biotech.* 13:79 (2013) pp. 1-16.
Staquicini, et al. "Design and proof-of-concept for targeted phage-based COVID-19 vaccination strategies with a streamlined cold-free supply chain" *bioRxiv* (2021) pp. 1-38.
Tao, et al. "Bacteriophage T4 nanoparticles for vaccine delivery against infectious diseases" *Adv. Drug Del. Rev.* 145 (2018) pp. 57-72.
ISA. "International Search Report & Written Opinion" PCT/US2021/022981 (dated Aug. 5, 2021) pp. 1-17.

*Primary Examiner* — Barry A Chestnut
(74) *Attorney, Agent, or Firm* — Dority & Manning, P.A.

(57) ABSTRACT

Engineered bacteriophage and methods of forming the bacteriophage are described. Multivalent bacteriophage are described that can include multiple different exogenous polypeptides at a surface of the capsid head. Vaccines and methods of forming and using vaccines are described. A vaccine can include an engineered bacteriophage that exhibits an immunogenic exogenous polypeptide at a surface of the bacteriophage. Multivalent bacteriophage and immunogenic bacteriophage are free of nucleic acids encoding the exogenous polypeptide(s).

21 Claims, 17 Drawing Sheets
Specification includes a Sequence Listing.

SEQUENCE LISTING

```
<160> NUMBER OF SEQ ID NOS: 15

<210> SEQ ID NO 1
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 1

```
Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
                100                 105                 110

Ser Gly Pro Val Gly Pro Gly Gly Ser Gly Ala Ser Arg Val Gln Pro
            115                 120                 125

Thr Glu Ser Ile Val Arg Phe Pro Asn Ile Thr Asn Leu Cys Pro Phe
130                 135                 140

Gly Glu Val Phe Asn Ala Thr Arg Phe Ala Ser Val Tyr Ala Trp Asn
145                 150                 155                 160

Arg Lys Arg Ile Ser Asn Cys Val Ala Asp Tyr Ser Val Leu Tyr Asn
                165                 170                 175

Ser Ala Ser Phe Ser Thr Phe Lys Cys Tyr Gly Val Ser Pro Thr Lys
            180                 185                 190

Leu Asn Asp Leu Cys Phe Thr Asn Val Tyr Ala Asp Ser Phe Val Ile
        195                 200                 205

Arg Gly Asp Glu Val Arg Gln Ile Ala Pro Gly Gln Thr Gly Lys Ile
    210                 215                 220

Ala Asp Tyr Asn Tyr Lys Leu Pro Asp Asp Phe Thr Gly Cys Val Ile
225                 230                 235                 240

Ala Trp Asn Ser Asn Asn Leu Asp Ser Lys Val Gly Gly Asn Tyr Asn
                245                 250                 255

Tyr Leu Tyr Arg Leu Phe Arg Lys Ser Asn Leu Lys Pro Phe Glu Arg
            260                 265                 270

Asp Ile Ser Thr Glu Ile Tyr Gln Ala Gly Ser Thr Pro Cys Asn Gly
        275                 280                 285

Val Glu Gly Phe Asn Cys Tyr Phe Pro Leu Gln Ser Tyr Gly Phe Gln
    290                 295                 300

Pro Thr Asn Gly Val Gly Tyr Gln Pro Tyr Arg Val Val Val Leu Ser
305                 310                 315                 320

Phe Glu Leu Leu His Ala Pro Ala Thr Val Cys Gly Pro Lys Lys
                325                 330                 335

<210> SEQ ID NO 2
<211> LENGTH: 110
<212> TYPE: PRT
<213> ORGANISM: Escherichia virus

<400> SEQUENCE: 2

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30
```

```
Pro Ala Met Thr Pro Leu Met Leu Asp Thr Ser Ser Arg Lys Leu Val
         35                  40                  45

Ala Trp Asp Gly Thr Thr Asp Gly Ala Ala Val Gly Ile Leu Ala Val
 50                  55                  60

Ala Ala Asp Gln Thr Ser Thr Thr Leu Thr Phe Tyr Lys Ser Gly Thr
 65                  70                  75                  80

Phe Arg Tyr Glu Asp Val Leu Trp Pro Glu Ala Ala Ser Asp Glu Thr
                 85                  90                  95

Lys Lys Arg Thr Ala Phe Ala Gly Thr Ala Ile Ser Ile Val
                100                 105                 110

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Ser Gly Pro Val Gly Pro Gly Gly Ser Gly Ala Ser
 1               5                  10

<210> SEQ ID NO 4
<211> LENGTH: 211
<212> TYPE: PRT
<213> ORGANISM: Severe acute respiratory syndrome coronavirus 2

<400> SEQUENCE: 4

Arg Val Gln Pro Thr Glu Ser Ile Val Arg Phe Pro Asn Ile Thr Asn
 1               5                  10                  15

Leu Cys Pro Phe Gly Glu Val Phe Asn Ala Thr Arg Phe Ala Ser Val
                20                  25                  30

Tyr Ala Trp Asn Arg Lys Arg Ile Ser Asn Cys Val Ala Asp Tyr Ser
             35                  40                  45

Val Leu Tyr Asn Ser Ala Ser Phe Ser Thr Phe Lys Cys Tyr Gly Val
         50                  55                  60

Ser Pro Thr Lys Leu Asn Asp Leu Cys Phe Thr Asn Val Tyr Ala Asp
 65                  70                  75                  80

Ser Phe Val Ile Arg Gly Asp Glu Val Arg Gln Ile Ala Pro Gly Gln
                 85                  90                  95

Thr Gly Lys Ile Ala Asp Tyr Asn Tyr Lys Leu Pro Asp Asp Phe Thr
                100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
        130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys
    210
```

<210> SEQ ID NO 5
<211> LENGTH: 427
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Gly Ser Gly Ala Ser Val Asn Leu Thr
        115                 120                 125

Thr Arg Thr Gln Leu Pro Pro Ala Tyr Thr Asn Ser Phe Thr Arg Gly
    130                 135                 140

Val Tyr Tyr Pro Asp Lys Val Phe Arg Ser Ser Val Leu His Ser Thr
145                 150                 155                 160

Gln Asp Leu Phe Leu Pro Phe Phe Ser Asn Val Thr Trp Phe His Ala
                165                 170                 175

Ile His Val Ser Gly Thr Asn Gly Thr Lys Arg Phe Asp Asn Pro Val
            180                 185                 190

Leu Pro Phe Asn Asp Gly Val Tyr Phe Ala Ser Thr Glu Lys Ser Asn
        195                 200                 205

Ile Ile Arg Gly Trp Ile Phe Gly Thr Thr Leu Asp Ser Lys Thr Gln
    210                 215                 220

Ser Leu Leu Ile Val Asn Asn Ala Thr Asn Val Val Ile Lys Val Cys
225                 230                 235                 240

Glu Phe Gln Phe Cys Asn Asp Pro Phe Leu Gly Val Tyr Tyr His Lys
                245                 250                 255

Asn Asn Lys Ser Trp Met Glu Ser Glu Phe Arg Val Tyr Ser Ser Ala
            260                 265                 270

Asn Asn Cys Thr Phe Glu Tyr Val Ser Gln Pro Phe Leu Met Asp Leu
        275                 280                 285

Glu Gly Lys Gln Gly Asn Phe Lys Asn Leu Arg Glu Phe Val Phe Lys
    290                 295                 300

Asn Ile Asp Gly Tyr Phe Lys Ile Tyr Ser Lys His Thr Pro Ile Asn
305                 310                 315                 320

Leu Val Arg Asp Leu Pro Gln Gly Phe Ser Ala Leu Glu Pro Leu Val
                325                 330                 335

Asp Leu Pro Ile Gly Ile Asn Ile Thr Arg Phe Gln Thr Leu Leu Ala
            340                 345                 350

Leu His Arg Ser Tyr Leu Thr Pro Gly Asp Ser Ser Ser Gly Trp Thr
        355                 360                 365
```

```
Ala Gly Ala Ala Ala Tyr Tyr Val Gly Tyr Leu Gln Pro Arg Thr Phe
        370             375                 380

Leu Leu Lys Tyr Asn Glu Asn Gly Thr Ile Thr Asp Ala Val Asp Cys
385             390                 395                 400

Ala Leu Asp Pro Leu Ser Glu Thr Lys Cys Thr Leu Lys Ser Phe Thr
            405                 410                 415

Val Glu Lys Gly Ile Tyr Gln Thr Ser Asn Phe
            420                 425

<210> SEQ ID NO 6
<211> LENGTH: 285
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Gly Ser Gly Ala Ser Ser Thr Asn Leu
        115                 120                 125

Val Lys Asn Lys Cys Val Asn Phe Asn Phe Asn Gly Leu Thr Gly Thr
    130                 135                 140

Gly Val Leu Thr Glu Ser Asn Lys Lys Phe Leu Pro Phe Gln Gln Phe
145                 150                 155                 160

Gly Arg Asp Ile Ala Asp Thr Thr Asp Ala Val Arg Asp Pro Gln Thr
                165                 170                 175

Leu Glu Ile Leu Asp Ile Thr Pro Cys Ser Phe Gly Gly Val Ser Val
            180                 185                 190

Ile Thr Pro Gly Thr Asn Thr Ser Asn Gln Val Ala Val Leu Tyr Gln
        195                 200                 205

Asp Val Asn Cys Thr Glu Val Pro Val Ala Ile His Ala Asp Gln Leu
    210                 215                 220

Thr Pro Thr Trp Arg Val Tyr Ser Thr Gly Ser Asn Val Phe Gln Thr
225                 230                 235                 240

Arg Ala Gly Cys Leu Ile Gly Ala Glu His Val Asn Asn Ser Tyr Glu
                245                 250                 255

Cys Asp Ile Pro Ile Gly Ala Gly Ile Cys Ala Ser Tyr Gln Thr Gln
            260                 265                 270

Thr Asn Ser Pro Arg Arg Ala Arg Ser Val Ala Ser Gln
        275                 280                 285
```

-continued

<210> SEQ ID NO 7
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Ser Gly Ala Ser Ile Ile Ala
        115                 120                 125

Tyr Thr Met Ser Leu Gly Ala Glu Asn Ser Val Ala Tyr Ser Asn Asn
130                 135                 140

Ser Ile Ala Ile Pro Thr Asn Phe Thr Ile Ser Val Thr Thr Glu Ile
145                 150                 155                 160

Leu Pro Val Ser Met Thr Lys Thr Ser Val Asp Cys Thr Met Tyr Ile
                165                 170                 175

Cys Gly Asp Ser Thr Glu Cys Ser Asn Leu Leu Leu Gln Tyr Gly Ser
            180                 185                 190

Phe Cys Thr Gln Leu Asn Arg Ala Leu Thr Gly Ile Ala Val Glu Gln
        195                 200                 205

Asp Lys Asn Thr Gln Glu Val Phe Ala Gln Val Lys Gln Ile Tyr Lys
    210                 215                 220

Thr Pro Pro Ile Lys Asp Phe Gly Gly Phe Asn Phe Ser Gln Ile Leu
225                 230                 235                 240

Pro Asp Pro Ser Lys Pro Ser Lys Arg Ser Phe Ile Glu Asp Leu Leu
                245                 250                 255

Phe Asn Lys Val Thr Leu Ala Asp Ala Gly Phe Ile Lys Gln Tyr Gly
            260                 265                 270

Asp Cys Leu Gly Asp Ile Ala Ala Arg Asp Leu Ile Cys Ala Gln Lys
        275                 280                 285

Phe Asn Gly Leu Thr Val Leu Pro Pro Leu Leu Thr Asp Glu Met Ile
    290                 295                 300

Ala Gln Tyr Thr Ser Ala Leu Leu Ala Gly Thr Ile Thr Ser Gly Trp
305                 310                 315                 320

Thr Phe Gly Ala Gly Ala Ala Leu Gln Ile Pro Phe Ala Met Gln Met
                325                 330                 335

Ala Tyr Arg Phe Asn Gly Ile Gly Val Thr Gln Asn Val Leu Tyr Glu
            340                 345                 350

Asn Gln Lys Leu Ile Ala Asn Gln Phe Asn Ser Ala Ile Gly Lys Ile
            355                 360                 365

Gln Asp Ser Leu Ser Ser Thr Ala Ser Ala Leu Gly Lys Leu Gln Asp
    370                 375                 380

<210> SEQ ID NO 8
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Gly Ser Gly Ala Ser Val Val Asn Gln
        115                 120                 125

Asn Ala Gln Ala Leu Asn Thr Leu Val Lys Gln Leu Ser Ser Asn Phe
    130                 135                 140

Gly Ala Ile Ser Ser Val Leu Asn Asp Ile Leu Ser Arg Leu Asp Lys
145                 150                 155                 160

Val Glu Ala Glu Val Gln Ile Asp Arg Leu Ile Thr Gly Arg Leu Gln
                165                 170                 175

Ser Leu Gln Thr Tyr Val Thr Gln Gln Leu Ile Arg Ala Ala Glu Ile
            180                 185                 190

Arg Ala Ser Ala Asn Leu Ala Ala Thr Lys Met Ser Glu Cys Val Leu
        195                 200                 205

Gly Gln Ser Lys Arg Val Asp Phe Cys Gly Lys Gly Tyr His Leu Met
    210                 215                 220

Ser Phe Pro Gln Ser Ala Pro His Gly Val Val Phe Leu His Val Thr
225                 230                 235                 240

Tyr Val Pro Ala Gln Glu Lys Asn Phe Thr Thr Ala Pro Ala Ile Cys
                245                 250                 255

His Asp Gly Lys Ala His Phe Pro Arg Glu Gly Val Phe Val Ser Asn
            260                 265                 270

Gly Thr His Trp Phe Val Thr Gln Arg Asn Phe Tyr Glu Pro Gln Ile
        275                 280                 285

Ile Thr Thr Asp Asn Thr Phe Val Ser Gly Asn Cys Asp Val Val Ile
    290                 295                 300

Gly Ile Val Asn Asn Thr Val Tyr Asp Pro Leu Gln Pro Glu Leu Asp
305                 310                 315                 320

Ser Phe Lys Glu Glu Leu Asp Lys Tyr Phe Lys Asn His Thr Ser Pro
                325                 330                 335

```
Asp Val Asp Leu Gly Asp Ile Ser Gly Ile Asn Ala Ser Val Val Asn
                340                 345                 350

Ile Gln Lys Glu Ile Asp Arg Leu Asn Glu Val Ala Lys Asn Leu Asn
            355                 360                 365

Glu Ser Leu Ile Asp Leu Gln Glu Leu Gly Lys Tyr Glu Gln Tyr Ile
        370                 375                 380

Lys Trp Pro
385

<210> SEQ ID NO 9
<211> LENGTH: 423
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Gly Ser Gly Ala Ser Met Ser Asp Asn
        115                 120                 125

Gly Pro Gln Asn Gln Arg Asn Ala Pro Arg Ile Thr Phe Gly Gly Pro
    130                 135                 140

Ser Asp Ser Thr Gly Ser Asn Gln Asn Gly Glu Arg Ser Gly Ala Arg
145                 150                 155                 160

Ser Lys Gln Arg Arg Pro Gln Gly Leu Pro Asn Asn Thr Ala Ser Trp
                165                 170                 175

Phe Thr Ala Leu Thr Gln His Gly Lys Glu Asp Leu Lys Phe Pro Arg
            180                 185                 190

Gly Gln Gly Val Pro Ile Asn Thr Asn Ser Ser Pro Asp Asp Gln Ile
        195                 200                 205

Gly Tyr Tyr Arg Arg Ala Thr Arg Arg Ile Arg Gly Gly Asp Gly Lys
    210                 215                 220

Met Lys Asp Leu Ser Pro Arg Trp Tyr Phe Tyr Tyr Leu Gly Thr Gly
225                 230                 235                 240

Pro Glu Ala Gly Leu Pro Tyr Gly Ala Asn Lys Asp Gly Ile Ile Trp
                245                 250                 255

Val Ala Thr Glu Gly Ala Leu Asn Thr Pro Lys Asp His Ile Gly Thr
            260                 265                 270

Arg Asn Pro Ala Asn Asn Ala Ala Ile Val Leu Gln Leu Pro Gln Gly
        275                 280                 285

Thr Thr Leu Pro Lys Gly Phe Tyr Ala Glu Gly Ser Arg Gly Gly Ser
    290                 295                 300
```

```
                                      -continued

Gln Ala Ser Ser Arg Ser Ser Arg Ser Arg Asn Ser Ser Arg Asn
305                 310                 315                 320

Ser Thr Pro Gly Ser Ser Arg Gly Thr Ser Pro Ala Arg Met Ala Gly
            325                 330                 335

Asn Gly Gly Asp Ala Ala Leu Ala Leu Leu Leu Asp Arg Leu Asn
            340                 345                 350

Gln Leu Glu Ser Lys Met Ser Gly Lys Gly Gln Gln Gln Gly Gln
        355                 360                 365

Thr Val Thr Lys Lys Ser Ala Ala Glu Ala Ser Lys Lys Pro Arg Gln
370                 375                 380

Lys Arg Thr Ala Thr Lys Ala Tyr Asn Val Thr Gln Ala Phe Gly Arg
385                 390                 395                 400

Arg Gly Pro Glu Gln Thr Gln Gly Asn Phe Gly Asp Gln Glu Leu Ile
                405                 410                 415

Arg Gln Gly Thr Asp Tyr Lys
            420

<210> SEQ ID NO 10
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Gly Ser Gly Ala Ser His Trp Pro Gln
        115                 120                 125

Ile Ala Gln Phe Ala Pro Ser Ala Ser Ala Phe Phe Gly Met Ser Arg
    130                 135                 140

Ile Gly Met Glu Val Thr Pro Ser Gly Thr Trp Leu Thr Tyr Thr Gly
145                 150                 155                 160

Ala Ile Lys Leu Asp Asp Lys Asp Pro Asn Phe Lys Asp Gln Val Ile
                165                 170                 175

Leu Leu Asn Lys His Ile Asp Ala Tyr Lys Thr Phe Pro Pro Thr Glu
            180                 185                 190

Pro Lys Lys Asp Lys Lys Lys Ala Asp Glu Thr Gln Ala Leu Pro
        195                 200                 205

Gln Arg Gln Lys Lys Gln Gln Thr Val Thr Leu Leu Pro Ala Ala Asp
    210                 215                 220
```

```
Leu Asp Asp Phe Ser Lys Gln Leu Gln Gln Ser Met Ser Ser Ala Asp
225                 230                 235                 240

Ser Thr Gln Ala

<210> SEQ ID NO 11
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Ser Gly Ala Ser Arg Val Val Pro
        115                 120                 125

Ser Gly Asp Val Val Arg Phe Pro Asn Ile Thr Asn Leu Cys Pro Phe
130                 135                 140

Gly Glu Val Phe Asn Ala Thr Lys Phe Pro Ser Val Tyr Ala Trp Glu
145                 150                 155                 160

Arg Lys Lys Ile Ser Asn Cys Val Ala Asp Tyr Ser Val Leu Tyr Asn
                165                 170                 175

Ser Thr Phe Phe Ser Thr Phe Lys Cys Tyr Gly Val Ser Ala Thr Lys
            180                 185                 190

Leu Asn Asp Leu Cys Phe Ser Asn Val Tyr Ala Asp Ser Phe Val Val
        195                 200                 205

Lys Gly Asp Asp Val Arg Gln Ile Ala Pro Gly Gln Thr Gly Val Ile
210                 215                 220

Ala Asp Tyr Asn Tyr Lys Leu Pro Asp Asp Phe Met Gly Cys Val Leu
225                 230                 235                 240

Ala Trp Asn Thr Arg Asn Ile Asp Ala Thr Ser Thr Gly Asn Tyr Asn
                245                 250                 255

Tyr Lys Tyr Arg Tyr Leu Arg His Gly Lys Leu Arg Pro Phe Glu Arg
            260                 265                 270

Asp Ile Ser Asn Val Pro Phe Ser Pro Asp Gly Lys Pro Cys Thr Pro
        275                 280                 285

Pro Ala Leu Asn Cys Tyr Trp Pro Leu Asn Asp Tyr Gly Phe Tyr Thr
290                 295                 300

Thr Thr Gly Ile Gly Tyr Gln Pro Tyr Arg Val Val Val Leu Ser Phe
305                 310                 315                 320

Glu Leu Leu Asn Ala Pro Ala Thr Val Cys Gly Pro Lys Leu
                325                 330
```

<210> SEQ ID NO 12
<211> LENGTH: 352
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Ser Gly Ala Ser Glu Ala Lys Pro
        115                 120                 125

Ser Gly Ser Val Val Glu Gln Ala Glu Gly Val Glu Cys Asp Phe Ser
130                 135                 140

Pro Leu Leu Ser Gly Thr Pro Pro Gln Val Tyr Asn Phe Lys Arg Leu
145                 150                 155                 160

Val Phe Thr Asn Cys Asn Tyr Asn Leu Thr Lys Leu Leu Ser Leu Phe
                165                 170                 175

Ser Val Asn Asp Phe Thr Cys Ser Gln Ile Ser Pro Ala Ala Ile Ala
            180                 185                 190

Ser Asn Cys Tyr Ser Ser Leu Ile Leu Asp Tyr Phe Ser Tyr Pro Leu
        195                 200                 205

Ser Met Lys Ser Asp Leu Ser Val Ser Ser Ala Gly Pro Ile Ser Gln
    210                 215                 220

Phe Asn Tyr Lys Gln Ser Phe Ser Asn Pro Thr Cys Leu Ile Leu Ala
225                 230                 235                 240

Thr Val Pro His Asn Leu Thr Thr Ile Thr Lys Pro Leu Lys Tyr Ser
                245                 250                 255

Tyr Ile Asn Lys Cys Ser Arg Leu Leu Ser Asp Asp Arg Thr Glu Val
            260                 265                 270

Pro Gln Leu Val Asn Ala Asn Gln Tyr Ser Pro Cys Val Ser Ile Val
        275                 280                 285

Pro Ser Thr Val Trp Glu Asp Gly Asp Tyr Tyr Arg Lys Gln Leu Ser
    290                 295                 300

Pro Leu Glu Gly Gly Gly Trp Leu Val Ala Ser Gly Ser Thr Val Ala
305                 310                 315                 320

Met Thr Glu Gln Leu Gln Met Gly Phe Gly Ile Thr Val Gln Tyr Gly
                325                 330                 335

Thr Asp Thr Asn Ser Val Cys Pro Lys Leu Glu Phe Ala Asn Asp Thr
            340                 345                 350
```

<210> SEQ ID NO 13
<211> LENGTH: 278
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 13

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Gly Ser Gly Ala Ser Asp Asp Asn Val
        115                 120                 125

Leu Pro Glu Thr Tyr Val Ala Leu Pro Ile Tyr Tyr Gln His Thr Asp
    130                 135                 140

Ile Asn Phe Thr Ala Thr Ala Ser Phe Gly Gly Ser Cys Tyr Val Cys
145                 150                 155                 160

Lys Pro His Gln Val Asn Ile Ser Leu Asn Gly Asn Thr Ser Val Cys
                165                 170                 175

Val Arg Thr Ser His Phe Ser Ile Arg Tyr Ile Tyr Asn Arg Val Lys
            180                 185                 190

Ser Gly Ser Pro Gly Asp Ser Ser Trp His Ile Tyr Leu Lys Ser Gly
        195                 200                 205

Thr Cys Pro Phe Ser Phe Ser Lys Leu Asn Asn Phe Gln Lys Phe Lys
    210                 215                 220

Thr Ile Cys Phe Ser Thr Val Glu Val Pro Gly Ser Cys Asn Phe Pro
225                 230                 235                 240

Leu Glu Ala Thr Trp His Tyr Thr Ser Tyr Thr Ile Val Gly Ala Leu
                245                 250                 255

Tyr Val Thr Trp Ser Glu Gly Asn Ser Ile Thr Gly Val Pro Tyr Pro
            260                 265                 270

Val Ser Gly Ile Arg Glu
        275

<210> SEQ ID NO 14
<211> LENGTH: 279
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 14

```
Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Gly Gly
            100                 105                 110

Ser Gly Pro Val Gly Pro Gly Gly Ser Gly Ala Ser Gln Pro Val Glu
        115                 120                 125

Leu Pro Val Ser Ile Val Ser Leu Pro Val Tyr His Lys His Thr Phe
    130                 135                 140

Ile Val Leu Tyr Val Asn Phe Glu His Gln Arg Gly Pro Gly Lys Cys
145                 150                 155                 160

Tyr Asn Cys Arg Pro Ala Val Ile Asn Ile Thr Leu Ala Asn Phe Asn
                165                 170                 175

Glu Thr Lys Gly Pro Leu Cys Val Asp Thr Ser His Phe Thr Thr Gln
            180                 185                 190

Phe Val Asp Asn Val Lys Leu Ala Arg Trp Ser Ala Ser Ile Asn Thr
        195                 200                 205

Gly Asn Cys Pro Phe Ser Phe Gly Lys Val Ile Asn Phe Val Lys Phe
    210                 215                 220

Gly Ser Val Cys Phe Ser Leu Lys Tyr Ile Pro Gly Gly Cys Ala Met
225                 230                 235                 240

Pro Ile Met Ala Asn Leu Val Asn His Lys Ser His Asn Ile Gly Ser
                245                 250                 255

Leu Tyr Val Ser Trp Ser Asp Gly Asp Val Ile Thr Gly Val Pro Lys
            260                 265                 270

Pro Val Glu Gly Val Ser Ser
        275
```

<210> SEQ ID NO 15
<211> LENGTH: 270
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60
```

```
Ala Ala Asp Gln Thr Ser Thr Thr Leu Thr Phe Tyr Lys Ser Gly Thr
 65             70                  75                  80

Phe Arg Tyr Glu Asp Val Leu Trp Pro Glu Ala Ala Ser Asp Glu Thr
                 85                  90                  95

Lys Lys Arg Thr Ala Phe Ala Gly Thr Ala Ile Ser Ile Val Gly Gly
            100                 105                 110

Ser Gly Pro Val Gly Pro Gly Gly Ser Gly Ala Ser Gly Asp Gln Asn
            115                 120                 125

Pro Gln Ile Ala Ala His Val Ile Ser Glu Ala Ser Ser Lys Thr Thr
            130                 135                 140

Ser Val Leu Gln Trp Ala Glu Lys Gly Tyr Tyr Thr Met Ser Asn Asn
145             150                 155                 160

Leu Val Thr Leu Glu Asn Gly Lys Gln Leu Thr Val Lys Arg Gln Gly
                165                 170                 175

Leu Tyr Tyr Ile Tyr Ala Gln Val Thr Phe Cys Ser Asn Arg Glu Ala
                180                 185                 190

Ser Ser Gln Ala Pro Phe Ile Ala Ser Leu Cys Leu Lys Ser Pro Gly
            195                 200                 205

Arg Phe Glu Arg Ile Leu Leu Arg Ala Ala Asn Thr His Ser Ser Ala
            210                 215                 220

Lys Pro Cys Gly Gln Gln Ser Ile His Leu Gly Gly Val Phe Glu Leu
225             230                 235                 240

Gln Pro Gly Ala Ser Val Phe Val Asn Val Thr Asp Pro Ser Gln Val
                245                 250                 255

Ser His Gly Thr Gly Phe Thr Ser Phe Gly Leu Leu Lys Leu
                260                 265                 270
```

BACTERIOPHAGE-BASED VACCINES AND ENGINEERED BACTERIOPHAGE

CROSS REFERENCE TO RELATED APPLICATION

This application claims filing benefit of U.S. Provisional Patent Application Ser. No. 62/992,394 entitled, "Supervaccines," to Ghanbari et al., having a filing date of Mar. 20, 2020, which is incorporated herein by reference, and claims filing benefit of U.S. Provisional Patent Application Ser. No. 63/073,908 entitled, "Supervaccines," to Ghanbari et al., having a filing date Sep. 2, 2020, which is incorporated herein by reference.

SEQUENCE LISTING

This application contains a Sequence Listing which has been submitted electronically in ASCII format and is hereby incorporated by reference in its entirety. Said ASCII copy, created on May 17, 2021, is named ATHA-1_Sequence List.txt and is 39,323 bytes in size.

BACKGROUND

Infectious diseases are caused by micro-organisms such as bacteria, fungi and parasites, as well as by viruses. These agents can infect higher order eukaryotes, including humans, where they replicate within the host tissues. While many of these infectious agents are innocuous and even beneficial to the normal function of the host organism, many cause disease with symptoms that can range from mild to severe and in some instances may result in the death of the host organism.

Of particular interest among infectious diseases are viral diseases. Viruses are essentially non-living infectious agents consisting of a nucleic acid (DNA or RNA) encapsulated in a viral coat, often made from protein, glycoprotein and/or lipid. Upon transfer to the host organism, the virus binds to and obtains access to specific cells where it can utilize the host cellular machinery to replicate and produce large numbers of new viral particles. These new viral particles are subsequently released from the infected cell, often by lysis of the cell, and go on to infect other host cells. The viral DNA or RNA generally encodes for relatively few viral-specific proteins including structural proteins, proteins necessary for cellular attachment and entry as well as any viral specific enzymes required for replication (e.g. reverse transcriptase, integrase and/or a protease). Some viruses can integrate into the host genome and lie dormant for long periods of time, only to re-emerge much later in the host cell's lifetime. Viruses cause disease by disrupting normal cellular functions and often inducing strong inflammatory responses within the host organism. They may also carry toxins and/or transfer genetic sequences into the host cell's chromosomes.

The mammalian immune system is specially adapted to respond to viral infections. The immune system consists of three major arms: the innate immune system, the humoral immune response, and the cellular immune response. The innate immune response is initiated through a process called pattern recognition and includes the activation of a series of general protective measures affording initial protection from infection (e.g. inflammation) and promoting the activation of more specific responses (e.g. activation of professional antigen presenting cells). The humoral response evolves against a specific pathogen and involves the production by B-cells of immunoglobulins or antibodies with high specificity towards the pathogen. These antibodies will bind to specific antigens on the pathogen, coating it and resulting in its clearance from the host tissues. In the case of infected cells, the antibodies can attach to the infected host cell and activate the complement system to kill the infected cell. The cellular response consists of the activation of highly specific T-cells, including both cytotoxic and helper T-cells. Cytotoxic T-cells directly recognize infected host cells and initiate apoptotic mechanisms in them. Helper T-cells support the activation and maturation of both pathogen-specific B-cells and cytotoxic T-cells.

A number of factors are necessary to support a robust and lasting immune response. Early and rapid activation of the innate immune system is key to the activation of the more specific arms of the immune system. The innate immune system must support generalized control of the pathogen while the humoral and cellular immune responses develop, which can take anywhere from several days to weeks. While the inflammatory response is an important part of the innate immune response, if inflammation becomes too vigorous it can be detrimental to the host organism and may also prevent stimulation of the humoral and cellular responses. The humoral and cellular immune systems must be able to identify and target specific antigens within the framework of the pathogen that are distinct and different from the normal host antigens to which they have been tolerized. In the case of the humoral response, the goal is to produce antibodies capable of neutralizing the pathogen. In order to retain immunity to the pathogen in the future, mechanisms must be activated to convert the B- and T-cells to memory B- and T-cells. These memory cells can quickly be reactivated upon reinfection with the same pathogen allowing the immune system to skip the steps required to develop a specific immune response and thus clear new infection before it has a chance to take hold.

The goal of vaccination is to prime an individual's immune system to be prepared to respond to a pathogen. As noted above, once the immune system has been exposed to a pathogen it can retain memory of that pathogen and the specific B- and T-cells necessary to fight off the infection. As such, the immune response to reinfection is much more robust, rapid, and generally able to clear the infectious agent before it can cause illness and/or harm to the host. Vaccines expose the immune system to antigens derived from the pathogen, but ideally do not subject the individual to the disease caused by the pathogen. To be effective, a vaccine must elicit a sufficient immune response to directly target the ensuant pathogen, the response must be both specific and neutralizing, and ultimately embedded into immunologic memory.

A number of different approaches have been used for vaccination. Many vaccines are simply killed or attenuated versions of the pathogen itself or of a closely related pathogen. The obvious advantage to these forms of vaccination is that they best resemble the natural live/active pathogen and as such would be expected to elicit immune responses most directly targeted to the specific pathogen. At the same time, if not completely inactivated or weakened, these vaccines may cause the very disease they are intended to protect against. Furthermore, if the pathogen is not itself immunogenic enough to produce a sufficient immune response, this form of vaccination will be unlikely to perform any better than the pathogen. In general, inactivated pathogens will be less immunogenic as they cannot replicate in the host, will require multiple doses, and tend to elicit mostly humoral immune responses which diminish over time and therefore may require periodic supplemental booster doses.

A second vaccination modality utilizes a portion or subunit derived from the pathogen as an immunogen. Subunit vaccines may utilize a protein, toxoid, polysaccharide or conjugate directly derived from the pathogen or synthesized recombinantly. The strength of the immune response to these types of vaccines will vary and is dependent on the choice of the antigen as well as the mode in which it is presented. These vaccines will often require several doses to elicit the initial immune response and later boosts to maintain the immune response. Given the more limited nature of the immunogen, the response will be less polyclonal and may protect only against a single strain of the pathogen and/or may be less effective with rapidly evolving/mutating pathogens.

Recently, DNA and mRNA have been explored as modalities for vaccination. DNA and RNA vaccines have only recently begun to be approved for use, and these modalities have shown efficacy in animal studies and are currently being investigated in numerous human clinical trials for wider use. The advantages of nucleic acid-based vaccines are the ease of manufacture and speed to new vaccine design. Like subunit vaccines these tend to target single proteins present within the pathogen. To function, the DNA or RNA must be taken up by host cells and the encoded gene must be transcribed and/or translated to express the protein within the host cell. Expression in any cell type may be sufficient to induce antibody responses, however specific expression in professional antigen presenting cells is likely required to elicit T-cell help and to induce immune memory.

Adjuvants are often used to enhance the immune response to a vaccine and without the addition of adjuvant many vaccines do not produce strong immune responses. In general, adjuvants cause localized inflammation and as such activate the innate immune system. Of the numerous activities of the innate immune response, perhaps the most important is the activation and stimulation of professional antigen presenting cells that are required to display foreign antigens to T-cells, especially T-helper cells. Adjuvants are thought to be particularly important for subunit vaccines. Caution is required, however, as some adjuvants can induce levels of inflammation that result in significant toxicities.

Bacteriophage (or more simply phage) are viruses that infect bacterial cells. These viruses consist of a protein coat which encapsulates a DNA or RNA genome. When phage infect a bacterial cell, they can coopt the host bacterial system to produce large numbers of phage copies and ultimately lyse the bacterial cell, releasing the new phage to the surrounding environment.

Bacteriophage have been used to display peptide or protein fragments for various uses. For example, phage display systems have been used to map the epitopes of antibodies or to identify single chain fragments of antibodies (scFv) that bind to specific antigens. These phage display systems gain their selection power in part from the ability to display many copies of a protein on the surface of the phage. By way of example, when using bacteriophage lambda ($\lambda$), the displayed protein is often engineered as an extension of the phage gpD coat protein. Greater than 400 copies of the gpD protein are used by the phage to construct its coat and as such as many as 400 copies of the requisite protein can be displayed on the phage surface. Moreover, displayed proteins can be quite large. For instance, in the case of bacteriophage $\lambda$, proteins of greater than 300 amino acids can be displayed without disrupting the ability of the phage coat to form.

This ability of phage to present on their surfaces large numbers of a protein or protein fragment qualifies them as bio-nanoparticles (BNPs). The use of phage as BNPs is especially advantageous as compared to other synthetic nanoparticles or bio-nanoparticles as phage are simple to genetically engineer and are easy to purify. Furthermore, phage can be produced at extremely high-yield in readily available bio-fermenters. As such, the development and manufacture processes can be rapid and highly cost-effective. In vivo, phage are known to have long half-lives and their size allows for easy tissue penetration. In general, phage have demonstrated only low levels of immunogenicity in mammals, including humans, likely due to early exposure and partial acquired immune tolerance due to the abundance of phage in the natural environment.

While the above describes improvement in the art, room for added improvement exists. For instance, phage for use in applications, such as vaccination applications, could be of great benefit in the art.

SUMMARY

According to one embodiment, disclosed is an engineered multivalent bacteriophage. For instance, an engineered multivalent bacteriophage can include a first fusion coat protein that includes a first exogenous polypeptide directly or indirectly fused to a first coat protein of the bacteriophage and a second fusion coat protein that includes a second exogenous polypeptide that can be of the same or a different type of exogenous polypeptide as the first exogenous polypeptide directly or indirectly fused to a second coat protein of the bacteriophage that can be of the same or a different type of coat protein as the first coat protein. In embodiments, additional exogenous polypeptides (e.g., a third, fourth, fifth, etc. up to n, where n=the total number of coat proteins of a bacteriophage) directly or indirectly fused to a coat protein of the bacteriophage may be included. In addition, the engineered multivalent bacteriophage can be free of nucleic acid sequences encoding any of the exogenous polypeptides.

Also disclosed are methods that can be used to form an engineered multivalent bacteriophage. For instance, a method can include transfecting one or more expression plasmids into a bacterial cell followed by infection of the bacterial cell with a phage. The one or more expression plasmids can include nucleic acid sequences that encode fusion coat proteins resulting in their expression within the bacterium and subsequent incorporation in newly produced phage. For instance, one, two or more nucleic acid sequences that encode fusion coat proteins can be a component of a single expression plasmid or nucleic acid sequences that encode different fusion coat proteins can be components of multiple separate expression plasmids, respectively. These fusion coat proteins can each include one or more exogenous polypeptides that are directly or indirectly fused to a coat protein of the phage. The one or more expression plasmids also include regulatory sequences such that following the transfection, fusion coat proteins are transiently expressed by the bacterial cell. Upon infection with phage that may or may not themselves contain DNA sequences to express the native or wild type coat protein, engineered multivalent phage can be produced by the bacterial cell that include the fusion coat proteins and that are free of nucleic acid sequences encoding the exogenous polypeptides.

According to one embodiment, disclosed is a vaccine that includes an engineered bacteriophage. The engineered bacteriophage can include a fusion coat protein that in turn includes one or more exogenous polypeptides directly or indirectly fused to one or more types of coat proteins of the bacteriophage. The exogenous polypeptide can have a sequence that corresponds to or is derived from (e.g., a homologue of) an immunogenic protein of a pathogen, and the bacteriophage can be free of nucleic acid sequences encoding the exogenous polypeptide. The exogenous polypeptide can elicit an immune response in a subject. Also disclosed are vaccines that include a multivalent engineered bacteriophage in which the bacteriophage includes multiple different exogenous polypeptides, each of which can be involved in eliciting one or more aspects of an immune response in a subject.

Also disclosed is a method for forming a vaccine. For instance, a method can include transfecting a bacterial cell with an expression plasmid and infecting the bacterial cell with a phage. The expression plasmid can include a nucleic acid sequence that encodes a fusion coat protein. The fusion coat protein can include an exogenous polypeptide directly or indirectly fused to a coat protein of the phage. The exogenous polypeptide can correspond to or be derived from an immunogenic polypeptide of a pathogen and can elicit in immune response in a subject. The expression plasmid can also include regulatory sequences such that following the transfection, the fusion coat protein is transiently expressed by the bacterial cell. Upon the infection and the transfection, an engineered phage can be produced by the bacterial cell that includes the fusion coat protein and that is free of nucleic acid sequences encoding the exogenous polypeptide.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
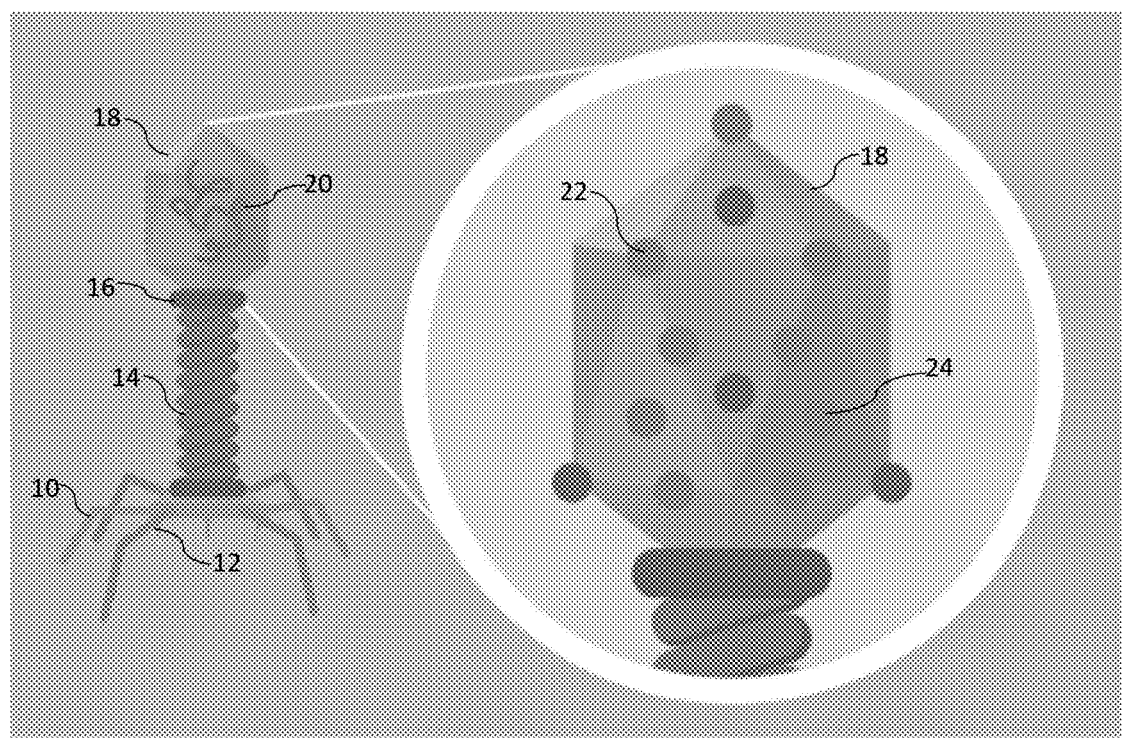
FIG. 1 schematically illustrates one embodiment of a multivalent bacteriophage as described herein.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

Disclosed herein are engineered bacteriophage and methods of forming the bacteriophage. In one embodiment, an engineered bacteriophage can be a multivalent bacteriophage and can include multiple different exogenous polypeptides at the surface of the capsid head. FIG. 1 schematically illustrates one embodiment of a multivalent bacteriophage. As illustrated, a multivalent bacteriophage can include typical bacteriophage components including tail fiber 10, spikes 12, and a sheath 14. A collar 16 typically separates the sheath 14 form the capsid head 18, which encases the bacteriophage DNA 20. The capsid head 18 is formed from a plurality of coat proteins, e.g., gpD, gpE and gpC coat protein in the case of bacteriophage λ. Multivalent bacteriophage as disclosed herein can include two or more different fusion coat proteins 22, 24 in the capsid head 18 that each include a different exogenous polypeptide at a terminal end of a coat protein. The coat protein components of the fusion coat proteins 22, 24 can be the same or different from one another.

Also disclosed are engineered bacteriophage that include two or more different fusion coat proteins in which the different fusion coat proteins include the same exogenous polypeptide at the end of different coat proteins of the phage. For instance, a first fusion coat protein can include an exogenous polypeptide directly or indirectly bonded to a terminal end of a first type of coat protein of the phage, and a second fusion coat protein can include the same exogenous polypeptide directly or indirectly bonded to a terminal end of a second type of coat protein of the phage. Methods of forming such engineered bacteriophage are also described.

An engineered bacteriophage can also include combinations of the above, e.g., multiple different fusion coat proteins that include combinations of fusion coat proteins with one or more different exogenous polypeptides directly or indirectly bonded to terminal ends of one or more different types of coat protein of the phage. Moreover, in some embodiments, a single fusion coat protein of an engineered phage can carry multiple exogenous polypeptides, which can be the same or different from one another, directly or indirectly bonded to a terminal end of the coat protein.

Also disclosed are vaccines incorporating an engineered bacteriophage. More specifically, a vaccine can include an engineered bacteriophage that exhibits one or more immunogenic exogenous polypeptides at a surface of the bacteriophage and that is free of nucleic acid encoding the exogenous polypeptide(s).

In one embodiment, a vaccine can include a multivalent bacteriophage that can include multiple different exogenous polypeptides involved in an immune response of a subject. The exogenous polypeptides can be derived from the same or different sources. For instance, a vaccine can include a multivalent bacteriophage that includes multiple different exogenous polypeptides developed from (e.g., corresponding to or derived from) one or more proteins of a single pathogen. For example, a first exogenous polypeptide can be developed from a first immunogenic portion of a pathogen protein and a second exogenous polypeptide can be developed from a second immunogenic portion of the same pathogen protein. In one embodiment the first and second exogenous polypeptides can correspond to or be derived from different proteins of the same pathogen. In one embodiment a vaccine can include a multivalent bacteriophage that includes multiple different exogenous polypeptides developed from proteins of different pathogens. In one embodiment, a vaccine can include a multivalent bacteriophage that includes one or more different exogenous polypeptides that can be directed to different aspects of an immune response. For instance, one exogenous polypeptide can be an immunogenic sequence that elicits an immune response in one or more of the innate, humoral, and cellular immune systems, and another exogenous polypeptide of the engineered bacteriophage can encourage retention of the immunity instilled by the immune response. Combinations of different types and sources of exogenous polypeptides can also be incorporated in a multivalent bacteriophage included in a vaccine as described.

Disclosed vaccines can be considered "supervaccines" that can provide immunity to one or multiple different pathogens that can be of the same or different types, e.g., different strains of the same virus type or different virus types. Disclosed vaccines incorporating engineered bacteriophage as described can induce and maintain strong immune responses against a broad number of different pathogenic proteins. In addition, and unlike previous generations of vaccines, disclosed vaccines do not incorporate live, attenuated, or killed pathogen (viral) particles and do not incorporate any pathogen DNA or RNA. Moreover, disclosed vaccines can be engineered, manufactured, distributed, and deployed rapidly and inexpensively.

Bacteriophage have a number of unique characteristics that make them a superior platform for a wide variety of applications, including vaccine construction and delivery. For instance, with regard to vaccine applications, phage are known to stimulate the innate immune response through pattern recognition and to specifically hone-in on professional antigen presenting cells, such as dendritic cells. Because phage stimulate the innate immune response directly, no added adjuvant is necessarily required in a vaccine formulation as disclosed, though an adjuvant can be included in some embodiments as discussed further herein.

The ability to display large copy numbers of exogenous polypeptides on the surface of a phage allows for the simultaneous delivery of a large amount of antigenic material to an antigen presenting cell. Furthermore, when displaying a viral coat protein or a fragment thereof on the surface of a phage, the phage becomes a physical mimic of the natural virus, making it effectively a virus-like particle (VLP).

Beneficially, disclosed formation methods can provide for phage that do not incorporate any foreign DNA or RNA and as such, there is no concern of transfer of DNA or RNA to a subject, which can be particularly beneficial in vaccination applications. The natural phage themselves are generally non-infective to mammalian cells and due to their abundance in nature, the mammalian immune system is likely pre-exposed to the natural phage and potentially even tolerized against anti-phage responses. Moreover, as the phage are bio-nanoparticles, they can optionally be irradiated prior to use to prevent any potential infectivity to a subject, for instance infectivity of symbiotic host prokaryotic organisms.

Disclosed engineered phage can include at least one exogenous polypeptide at a surface of the phage coat. As utilizes herein, the term "exogenous" refers to a material that originates external to and is not naturally found as a component of either the phage or the bacterial cell that is used to produce the engineered phage. As utilized herein, the term "polypeptide" generally refers to a polymeric molecule including two or more amino acid residues, which can include natural and synthetic amino acids as well as combinations thereof and includes proteins as well as fragments. As utilized herein, the term "fragment" generally refers to a continuous part of a full-length protein, with or without mutations, which is separate from and not in the context of a full length protein. A fragment may be a structural/topographical or functional subunit of a full length protein. In some embodiments, a fragment can have an amino acid sequence of about 15 or more amino acids, or about 20 or more amino acids of the parent full-length surface protein.

In one embodiment, an exogenous polypeptide can be developed from a protein of a pathogen. For instance, an exogenous polypeptide can correspond to or be derived from a whole or fragment of a protein of a pathogen. For example, an exogenous polypeptide can be identical to (e.g., correspond to) a pathogenic protein or an immunogenic fragment thereof or can be a functional mutant or homologue of a protein or a protein fragment. As utilized herein, the term "homologue" generally refers to a nucleotide or polypeptide sequence that differs from a reference sequence by modification(s) that do not affect the overall functioning of the sequence. For example, when considering polypeptide sequences, homologues include polypeptides having substitution of one amino acid at a given position in the sequence for another amino acid of the same class (e.g., amino acids that share characteristics of hydrophobicity, charge, pK or other conformational or chemical properties, e.g., valine for leucine, arginine for lysine, etc.). Homologues can include one or more substitutions, deletions, or insertions, located at positions of the sequence that do not alter the conformation or folding of a polypeptide to the extent that the biological activity of the polypeptide is destroyed. Examples of possible homologues include polypeptide sequences and nucleic acids encoding polypeptide sequences that include substitution of one non-polar (hydrophobic) residue such as isoleucine, valine, leucine or methionine for another; the substitution of one polar (hydrophilic) residue for another such as between arginine and lysine, between glutamine and asparagine, or between threonine and serine; the substitution of one basic residue such as lysine, arginine or histidine for another; the substitution of one acidic residue, such as aspartic acid or glutamic acid for the another; or the use of a chemically derivatized residue in place of a non-derivatized residue, as long as the homolog displays substantially similar biological activity to the reference sequence.

Formation methods of disclosed bacteriophage include transfecting a bacterial cell with an expression plasmid that includes a nucleic acid sequence encoding a fusion phage coat protein. An expression plasmid can be produced by recombinant DNA technology as known. A fusion coat protein encoded by the expression plasmid can include a native or wild type phage coat protein with an added N- or C-terminal extension (e.g., a full pathogenic protein or fragment thereof) that can be directly or indirectly fused to a terminus of the coat protein (e.g., indirectly fused by inclusion of a spacer between the two or by inclusion of multiple exogenous pathogenic proteins or fragments thereof on a single coat protein). An expression plasmid can be transfected into the bacterial cell prior to or in conjunction with infection of the bacterial cell with a phage that naturally includes the coat protein of the fusion coat protein encoded by the expression plasmid.

An expression plasmid can include a DNA sequence encoding a phage coat protein ligated to a DNA sequence encoding the selected exogenous polypeptide(s) such that the exogenous polypeptide sequence(s) is in frame with the coat protein sequence. DNA encoding a short linker sequence may be placed between the sequences if desired, for instance to achieve successful expression.

The coat protein encoded in the expression plasmid and expressed with an exogenous polypeptide as a fusion coat protein can vary depending upon the phage type. The phage may be any bacteriophage known to those skilled in the art, including but not limited to λ, M13, T4, T7, φX174.

By way of example, when forming an engineered λ phage, an expression plasmid can include DNA encoding one or more fusion coat proteins based on one or more of the gpD, gpE or gpC coat proteins in conjunction with the encoding of one or more exogenous polypeptides in any combination. For example DNA of one or more plasmids can encode a first exogenous polypeptide in conjunction with a gpD coat protein as well as encoding that same exogenous polypeptide in conjunction with a gpE coat protein, DNA of one or more plasmids can encode a first exogenous polypeptide in conjunction with a gpD coat protein as well as a second, different exogenous polypeptide in conjunction with a gpD coat protein, can encode a first exogenous polypeptide in conjunction with a gpD coat protein as well as a second, different exogenous polypeptide in conjunction with a different, e.g., gpE, coat protein, or any combination thereof.

If an engineered M13 phage is to be formed, one or more of the pVIII, pIII, pVI, pVII or pIX proteins can generally be encoded in an expression plasmid in conjunction with one or more exogenous polypeptides. Similarly, the gp23 and/or gp24 proteins can generally be encoded when forming an engineered T4 bacteriophage and the gp10A and/or gp10B proteins can be encoded in an expression plasmid when forming an engineered T7 phage. For phage φX174 the gpF and/or gpG proteins can generally be encoded in conjunction with one or more exogenous polypeptides.

A hybrid DNA sequence encoding a fusion coat protein can be placed into a bacterial expression plasmid under the control of a suitable bacterial expression promoter. A promoter can be an inducible promoter, a copy of a native phage promoter or any promoter deemed appropriate by one skilled in the art. The expression plasmid can be one that provides for transient expression of the fused coat protein in the bacterial cell. Transient expression systems have been used as tools of recombinant technology for many years and as such is not described in detail herein By way of example and without limitation, suitable transient expression systems can include the pET Duet family of vectors from Novagen/EMDMillipore.

In forming a multivalent bacteriophage, in one embodiment, a single expression plasmid can include multiple different hybrid DNA sequences, each of which encode a different fusion coat protein. For instance, in one embodiment, an expression plasmid can include one or more variant copies of a hybrid DNA sequence, each of which encoding a different exogenous polypeptide extension of the same fusion coat protein. The different exogenous polypeptide sequences can be different variants of a natural polypeptide (e.g., corresponding to the natural polypeptide and one or more homologues or mutants of the natural polypeptide) or different polypeptides all together. In another embodiment, multiple different plasmids may be used in forming a multivalent bacteriophage, with different plasmids including different hybrid DNA sequences that encode for a different fusion coat protein (e.g., different by the exogenous polypeptide extension, the phage coat protein, or both).

In another embodiment, an engineered bacteriophage may display only a single exogenous polypeptide sequence, but may include multiple different fusion coat proteins, with the exogenous polypeptide sequence as a component of different fusion coat proteins that incorporate different types of coat proteins of the native phage.

When using different expression plasmids to carry different fusion coat protein DNA, the regulatory components of the expression plasmids can be the same or differ from one another. For instance, in one embodiment, different expression plasmids can be essentially the same as one another other than the fusion coat protein DNA sequences. In one embodiment, different selection markers can be incorporated on the different expression plasmids, which can be used to ensure that selected production bacteria have incorporated all plasmid types. In one embodiment, different plasmids or different expression components of a single plasmid can incorporate different promotors driving expression of the fusion coat proteins, for instance, different strength promoters, thus allowing for the fusion coat proteins with different exogenous polypeptide extensions to be produced at varying levels which can also allow for incorporation of the different fusion coat proteins into an engineered phage at different ratios.

Exogenous polypeptide sequences chosen for inclusion in a fusion coat protein may be derived from any source and can include complete proteins, protein fragments, mutants, or homologues thereof. In one embodiment, an exogenous polypeptide sequence can be an immunogenic sequence developed from a viral specific protein. In one embodiment, an exogenous polypeptide can correspond to a sequence found in a coat protein of an infectious agent (e.g., a virus). It should be understood, however, that an immunogenic exogenous polypeptide is in no way limited to one derived from a viral coat protein and may correspond to or be derived from any other immunogenic protein of a pathogen.

In one particular embodiment, an exogenous immunogenic polypeptide can be one that is a known epitope for neutralizing antibodies produced in subjects previously known to have had immune responses to the pathogen, where this information is available.

DNA sequences incorporated in an expression plasmid can encode an exogenous polypeptide of any length. For instance, a DNA sequence of an expression plasmid can encode an exogenous polypeptide that is about 12 amino acids or greater in length, for instance about 15 amino acids or greater, about 50 amino acids or greater, about 100 amino acids or greater, or about 150 amino acids or greater in length in some embodiments. In one embodiment, a DNA sequence of an expression plasmid can encode an exogenous polypeptide that is about 500 amino acids or less in length, for instance about 450 amino acids or less, about 400 amino acids or less, about 350 amino acids or less, or about 300 amino acids or less in length in some embodiments. The exogenous polypeptide of a fusion coat protein can be of any length provided it does not interfere with the incorporation of the fusion coat protein in the bacteriophage during formation thereof by the bacterial cell.

In one embodiment a multivalent bacteriophage can be engineered that can include multiple different fragments (or homologues thereof) of a single protein, for instance, when the natural protein of interest is large and incorporation of the entire protein sequence in a single fusion coat protein could interfere with bacteriophage formation.

A multivalent bacteriophage can include different exogenous sequences developed from a single protein, from different proteins of the same source (e.g., the same pathogen), or from different proteins from different sources. For instance, different exogenous polypeptides of a multivalent immunogenic bacteriophage as may be incorporated in a vaccine can be developed from a single or multiple proteins of a single virus strain, from multiple strains of a single virus family and/or from different viral families. For instance, a first exogenous polypeptide can be developed from the receptor binding domain of the spike protein of a coronavirus and a second exogenous polypeptide can be developed from a second, different domain of the spike protein.

It should be understood that exogenous polypeptides are not limited to those developed from viral pathogens, and other exogenous polypeptide types are encompassed herein. By way of example, an exogenous polypeptide can be developed from pathogens including, and without limitation to, bacterial pathogens, fungal pathogens, parasites, and/or viral pathogens. Pathogens encompassed herein can include, without limitation, coronavirus, influenza, HIV, HCV, HBV, HPV, dengue, Chikungunya, and West Nile. Moreover, exogenous polypeptides are not necessarily limited to those derived from pathogens, and engineered bacteriophage as disclosed herein, e.g., multivalent bacteriophage as described, can incorporate exogenous polypeptides developed from other proteinaceous sources, in addition to or instead of as vaccine agents.

By way of example, in one particular embodiment, an engineered bacteriophage can be a component of a vaccine against a coronavirus. Four major membrane surface proteins are known to be expressed on the surface of coronavirus virus particles, S, E, M, and N. In one embodiment, all four of these proteins or fragments thereof can be used to develop exogenous polypeptides on one or more different phage or on a single phage. In one embodiment one or more other types of coronavirus proteins can be used to develop an exogenous polypeptide, for instance in conjunction with one or more exogenous polypeptides developed from a surface protein. For example, SARS-CoV-2 proteins that can be utilized to develop an exogenous polypeptide can include, without limitation, spike, nucleocapsid, membrane, and/or envelope proteins. In one embodiment all proteins of a pathogen can be used to develop a plurality of different exogenous polypeptides displayed on a surface of one or more phage.

In one embodiment, multiple different membrane surface proteins of multiple strains and/or different types of pathogens can be displayed at a phage surface. For example, a multivalent engineered bacteriophage can display multiple different exogenous immunogenic polypeptides at the surface derived from one, multiple, or all known coronaviruses including, without limitation, SARS (e.g., SARS-CoV-1, SARS-CoV-2), MERS, HKU (e.g., HKU1), NL63, OC43, and/or 229E. Proteins as may be utilized in development of a vaccine as described herein can include, without limitation, SARS-CoV-1 S-protein RBD (e.g., amino acid residues 306-515), MERS S-protein RBD (e.g., amino acid residues 364-594), NL63 S-protein RBD (e.g., amino acid residues 465-618), HKU1 S-protein RBD (e.g., amino acid residues 310-610), OC43 S-protein RBD (e.g., amino acid residues 325-620) or 229E S-protein RBD (e.g., amino acid residues 271-435). Accession numbers for representative proteins as may be utilized in development of a vaccine include, without limitation, NP_073551.1 surface glycoprotein [Human coronavirus 229E], AFV53148.1 protein S [Human coronavirus NL63], YP_173238.1 spike glycoprotein [Human coronavirus HKU1], QDH43726.1 S [Human coronavirus OC43], QFQ59587.1 S [Middle East respiratory syndrome-related coronavirus], AAP13441.1 S protein [SARS coronavirus Urbani], and YP_009724390.1 surface glycoprotein [Severe acute respiratory syndrome coronavirus 2].

In one embodiment, an engineered bacteriophage can display one or more exogenous polypeptides developed from other viral pathogens such as influenzas, etc. In one embodiment, an engineered bacteriophage can display one or more exogenous polypeptides developed from different types of pathogens, for instance one or more exogenous polypeptides developed from one or more coronaviruses and one or more exogenous polypeptides developed from one or more influenzas.

In one embodiment, a single exogenous immunogenic polypeptide can be incorporated in one or more fusion coat protein(s) that can provide immunity to multiple different pathogens. For example, comparison of the sequences of all known members of a given virus type or strain (e.g., comparison of all known coronavirus sequences) can be used to determine mutational hotspots. A mutational hotspot as determined from such a comparison can then be used to develop a single exogenous immunogenic polypeptide that is common to all of the different members. Thus, immunization of a subject by use of the bacteriophage can elicit an immune response in the subject representative of all of the different members of the viral group. In one embodiment, upon determination of a such a mutational hotspot, random mutations can be generated covering this hotspot and these mutants can be used to develop multiple different exogenous proteins present on a multivariant phage which can then be incorporated in a vaccine that can potentially provide immunity against future mutants of the pathogen.

Exogenous polypeptides encoded by an expression plasmid can include polypeptides that trigger or are involved in any aspect of an immune response. For instance, in one embodiment, an exogenous polypeptide of an engineered phage can be involved in development of an immune response memory in a subject. For a vaccine to supply long-term protection against future infection, the initial B- and T-cell responses must mature, and a subset of these cells must be converted to memory cells. The maturation of memory B- and T-cells is dependent on the activation of certain signaling pathways within these cells. In the case of memory B-Cells, this signal is often activated through interaction with helper T-cells ($T_H2$) which engage B-cells through a surface protein on each of the cells; CD40L on the helper T-cell and CD40 on the B-cell. Conversion of cytotoxic T-cells to memory also occurs through signaling by certain cytokines released by helper T-cells ($T_H1$) (e.g. IFN-γ, IL-2, IL-10, TNF-α, TNF-β).

Thus, in one embodiment, exogenous polypeptides of a fusion coat protein can be developed from CD40L and/or $T_H1$-released cytokines. For instance, entire cytokines or fragments or homologues thereof can be present as an exogenous polypeptide of a fusion coat protein together with a second exogenous polypeptide that initiates an immune response in a subject. Upon immunization of a subject with a vaccine including such an engineered bacteriophage, CD40L together with antigen can be presented to B-cells, and the effects of $T_H2$ helper T-cells on B-cells can be mimicked resulting in conversion to memory B-cells. Similarly, presentation of one or more $T_H1$ released cytokines can promote proliferation of cytotoxic T-cells and conversion to the memory phenotype.

Memory-enhancing components can be a portion of an initial vaccination, e.g., present as a fusion coat protein in an engineered bacteriophage that also includes exogenous polypeptide(s) that initiate an immune response in a subject. Alternatively, an initial vaccination may employ antigenic exogenous polypeptide(s) without an added memory component and such can be incorporated in one or more booster vaccinations. In such an embodiment, an initial vaccine can stimulate an initial immune response and subsequently, during the boost phase, the cells would be stimulated towards the memory phenotype.

Upon development of one or more expression plasmids that include DNA encoding the one or more fusion coat proteins, the plasmid(s) can be transfected into a host bacterial cell. The host bacterial cell can be any suitable type that is also infectable by the phage that is to be the basis for the engineered phage product. For instance, when forming an engineered bacteriophage λ, the host bacterial cell can be an *E. coli* and an *E. coli* can thus be transfected with the expression plasmid(s) according to standard transfection practice. Suitable bacterial hosts for phage infection are known to those in the art.

In conjunction with or subsequent to the transfection of the host with the one or more expression plasmid(s), the host can be infected with the phage of choice. Depending upon the transfection/expression system utilized, additional components as necessary can be supplied to the bacterial host. For instance, if an inducible promoter is incorporated in the expression plasmid(s), the inducing agent can also be supplied to the bacterial host during phage infection.

Upon transfection and infection, the bacterial host can produce the engineered bacteriophage that incorporate the fusion coat proteins. Beneficially, because the fusion coat proteins are produced from plasmid(s) transiently expressed in the bacteria during phage production, the DNA encoding the exogenous polypeptide is not incorporated into the phage.

The amount of fusion coat proteins incorporated into an engineered bacteriophage can be controlled in one embodiment, for instance through selection of the promoter strength of an expression plasmid. Such an approach can be used to control relative amount of different fusion coat protein in a bacteriophage as well as relative amount of the natural, e.g., wild type, coat protein vs. the fusion coat protein. In such an embodiment, the natural phage coat protein upon which the fusion coat protein is based can be maintained to a controlled extent on the engineered phase. Thus, the engineered phage can include a portion of the coat protein lacking any fused exogenous polypeptide in addition to the fused coat protein.

In one embodiment, the bacterial cell can be infected with a knock-out phage in which the wild type coat protein expression has been silenced or deleted. In this case, all of the coat protein of the type incorporated in the expression plasmid (e.g., all gpD coat protein of a bacteriophage λ) can be present in the expressed engineered phage as fusion coat protein.

Following transfection and infection, a host bacteria can be grown until lysis of the bacteria. Once bacterial cell lysis has occurred, the phage can be purified and characterized using standard techniques. It should be noted that loss of infectivity by the modified phage is not a problem for the use of the engineered phage as a vaccine and can be advantageous in some embodiments.

Engineered phage as described can serve as bio-nanoparticles that are easily manufactured in bacterial cultures and that can be grown at large scale in standard bio-fermenters.

Following lysis, engineered bacteriophage may be purified by any number of methods known to those skilled in the art for bacteriophage purification. These methods include, but are not limited to polyethylene glycol (PEG) precipitation, tangential flow filtration, affinity chromatography, etc. Engineered bacteriophage may be further concentrated, devoided of bacterial endotoxins and characterized by standard methods known to those skilled in the art.

In those embodiments in which the engineered bacteriophage is developed for application in vaccines, vaccine formulation can be carried out to include the bacteriophage according to known vaccine formation protocols as are known to those skilled in the art. For instance, purified bacteriophage can be transferred into a buffered saline solution with commonly used preservatives and filter sterilized. Because of the high stability of bacteriophage, a vaccine incorporating an engineered immunogenic bacteriophage can be stable at ambient and room temperatures for long periods, e.g., one week to several months.

A vaccine can be prepared in one embodiment as an injectable, either as a liquid solution or suspension. A solid form suitable for solution in, or suspension in, liquid prior to injection may also be prepared. The preparation may also be emulsified, or the ingredients can be mixed with excipients that are pharmaceutically acceptable and compatible with the bacteriophage. Suitable excipients are, for example, saline or buffered saline (pH 7 to 8), or other physiologic, isotonic solutions that may also contain dextrose, glycerol or the like and combinations thereof. In addition, a vaccine can contain minor amounts of auxiliary substances such as wetting or emulsifying agents, pH buffering agents that can enhance the effectiveness of the vaccine.

A vaccine may optionally include an adjuvant. Examples of adjuvants can include but are not limited to: aluminum hydroxide, Freund's complete adjuvant (FCA or CFA), N-acetyl-muramyl-L-threonyl-D-isoglutamine (thr-MDP), N-acetylmuramyl-L-alanyl-D-isoglutaminyl-L-alanine-2-(1'-2'-dipalmitoyl-s-n-glycero-3-hydroxyphosphoryloxy)-ethylamine (CGP 19835A, referred to as MTP-PE), and TIBI, which contains three components extracted from bacteria, monophosphoryl lipid A, trehalose dimycolate and cell wall skeleton (MPL+TDM+CWS) in a 2% squalene/Tween 80 emulsion.

A vaccine can be delivered by any of the standard routes used for vaccination including but not limited to intramuscular, intravenous, subcutaneous, intradermal, etc. Of special interest is intradermal delivery as skin is known to contain a large number of cells of the innate and adaptive immune system that can provide a rapid and robust response to the vaccine. However, any route of administration can be used to deliver a vaccine to a subject and while a vaccine can be administered via intramuscular injection or intranasal administration, delivery methods are not limited to such routes. A vaccine can be applied or instilled into body cavities, absorbed through the skin (e.g., via a transdermal patch), inhaled, ingested, topically applied to tissue, or administered parenterally via, for instance, intravenous, peritoneal, or intraarterial administration.

A delivery device can be utilized that allows controlled or sustained release, such as a sponge, biocompatible meshwork, mechanical reservoir, or mechanical implant. Implants and devices as can be useful for administration of a vaccine have been described and are known in the art (see, e.g., U.S. Pat. Nos. 5,443,505 and 4,863,457, both of which are incorporated by reference herein). A vaccine can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate BHET), and/or a polylactic-glycolic acid.

An engineered phage can be used to vaccinate a subject either prophylactically to prevent infection with one or more targeted pathogen(s) or may be delivered therapeutically to enhance an individual's immune response to an existing infection.

The dosage of an immunogenic composition administered to a subject can depend on a number of factors, including the extent of any side-effects, the particular route of administration, and the like. The dose ideally comprises an "effective amount" of an immunogenic composition, i.e., a dose of immunogenic exogenous polypeptide carried on an engineered bacteriophage that can provoke a desired immune response in a subject. The desired immune response can entail production of antibodies, protection upon subsequent challenge, immune tolerance, immune cell activation, and the like.

Beneficially, a vaccine as described can require only a single vaccination in some embodiments and through the single vaccination can elicit a string immune response in a subject. In some embodiments, a vaccine as disclosed can be delivered to a subject multiple times over a course of vaccinations to boost the initial immune response. For instance, an initial vaccination can be followed with one or more boosters following a period of from about one week to about 6 months, e.g., from about two weeks to about three months, to boost the subject's initial immune response. Such a booster immunization can in some embodiments utilize an engineered phage that incorporates an exogenous polypeptide designed to memorialize the immune response in a subject. The present disclosure may be better understood with reference to the Examples set forth below.

Example 1

Coronaviruses utilize four major membrane structural proteins which are known to be expressed on the surface of or within the virus particles: Spike (S), Envelope (E), Membrane (M) and Nucleocapsid (N). Of these four viral proteins the S and N proteins are known to be highly immunogenic in infected individuals with active anti-viral immune responses. Natural antibodies against the S protein, and in particular against the receptor binding domain (RBD) of the S protein are known to be neutralizing.

In this example a bacteriophage was formed displaying S-RBD derived from SARS-CoV-2, the coronavirus that causes COVID-19 disease.

Initially, DNA encoding amino acids 319-529 of the SARS-CoV-2 Spike protein (accession number provided previously) were engineered such that the DNA sequence was attached to the 3' end of DNA encoding the lambda phage gpD protein with a short piece of DNA in between which codes for the amino acid sequence, GGSGPVGPGGSGAS (SEQ ID NO: 3). The engineered protein was expressed in bacteria simultaneously with lambda infection of the same bacterium. These bacteria produced a new engineered lambda phage (ATHR-M1) which incorporated the gpD-linker-SRBD protein together with natural phage gpD.

The fusion protein was constructed such that the S-RBD is fused to the gpD at the C-terminus of the gpD with a short flexible linker in between. The entire amino acid sequence of the fused protein is as follows:

```
                                 SEQ ID NO: 1
  1 MTSKETFTHYQPQGNSDPAHTATAPGGLSAKAPAMTPLMLDTSSRKLVAW    50

51 DGTTDGAAVGILAVAADQTSTTLTFYKSGTFRYEDVLWPEAASDETKKRT   100

101 AFAGTAISIVGGSGPVGPGGSGASRVQPTESIVRFPNITNLCPFGEVFNA   150

151 TRFASVYAWNRKRISNCVADYSVLYNSASFSTFKCYGVSPTKLNDLCFTN   200

201 VYADSFVIRGDEVRQIAPGQTGKIADYNYKLPDDFTGCVIAWNSNNLDSK   250

251 VGGNYNYLYRLFRKSNLKPFERDISTETYQAGSTPCNGVEGFNCYFPLQS   300

301 YGFQPTNGVGYQPYRVVVLSFELLHAPATVCGPKK                  335
```

Of the above sequence, residues 1-110 describe the gpD sequence (SEQ ID NO: 2), residues 111-124 are the linker (SEQ ID NO: 3, in italics), and residues 125-335 describe the S-RBD sequence (SEQ ID NO: 4, in bold). The same fonts are used to describe linker (italics) and protein fragments (bold) in other sequences encoding fusion proteins throughout this description.

Figure 2:
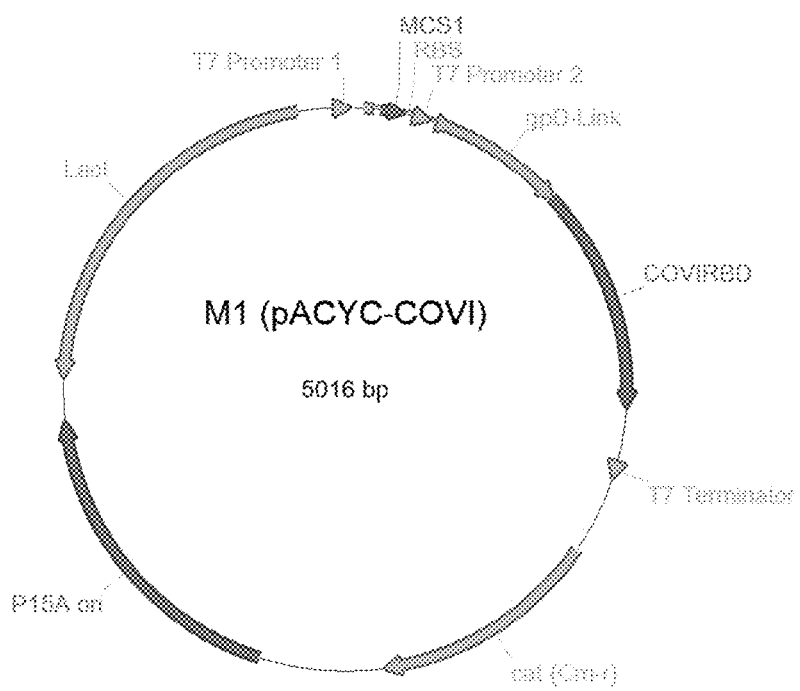
FIG. 2 illustrates an expression vector as may be utilized in forming an engineered phage as described herein.
Figure 3:
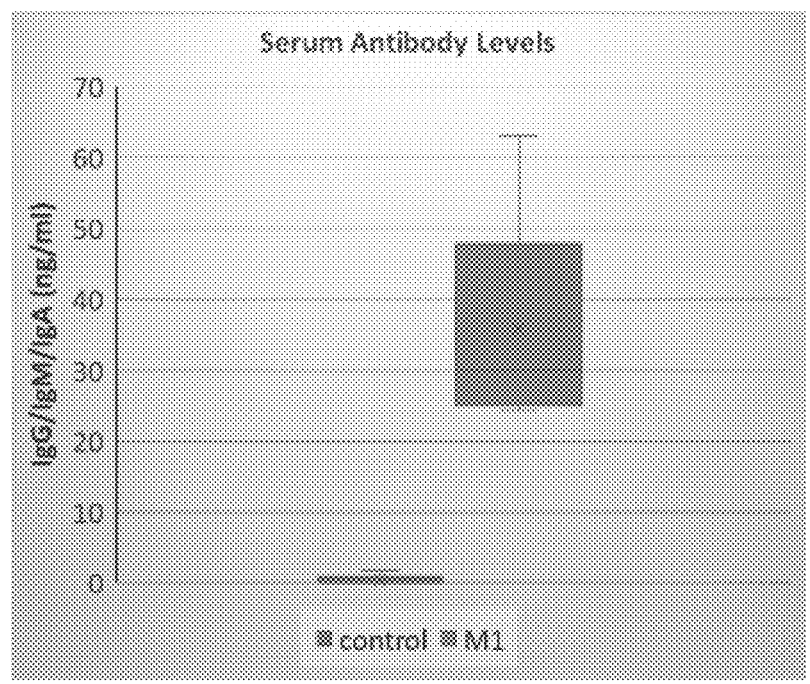
FIG. 3 graphically compares the serum antibody levels of subjects immunized with a vaccine comprising ATHR-M1 as described compared to control subjects.
Figure 4:
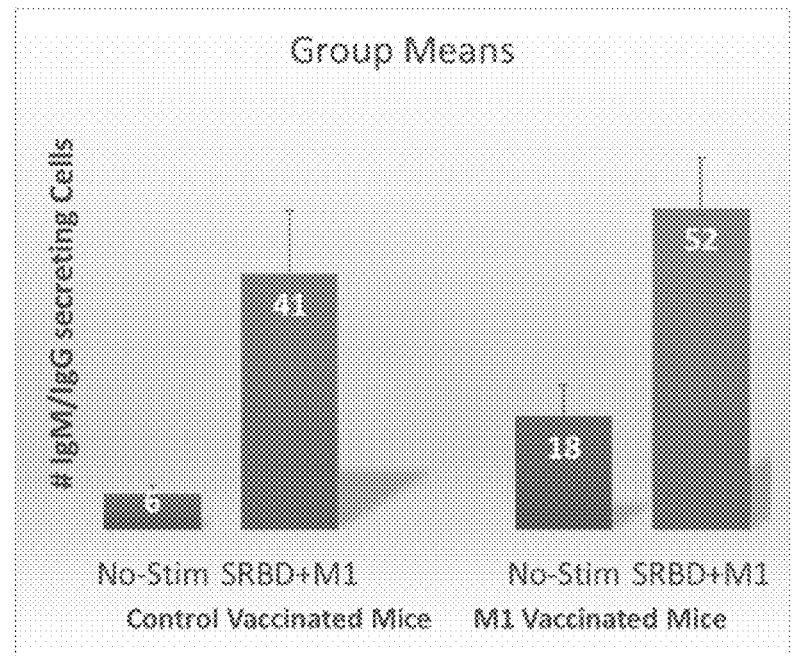
FIG. 4 graphically compares the B-cell responses of subjects immunized with a vaccine comprising ATHR-M1 as described compared to control subjects.

The nucleic acid sequence encoding the fusion protein was determined from the amino acid sequence and was optimized for codon usage in *E. coli* K12. The nucleic acid sequence was cloned into the expression vector pACYC-Duet-1 (Novagen) in the second multi-cloning site at the restriction site for NdeI (FIG. 2). The resultant plasmid was sequenced across all junctions to ensure proper construction. Expression was under a T7 promoter. The final vector, designated pACYC-COVI, was transfected into *E. coli* BL21 (DE3).

Expression of ATHR-M1 was achieved as follows: *E. coli* transfected with the pACYC-COVI expression vector were selected on chloramphenicol containing medium, grown to an $OD_{600}$=0.4-0.8 at 37° C., induced with IPTG and simultaneously infected with wildtype bacteriophage λ (ATCC 23724 B2) at an MOI of 1-10. Cultures were allowed to grow for 4-5 hours.

Phage were isolated by centrifugation of cultures at 10000×g to remove cells and cell debris. The supernatant was clarified through a 0.45μ filter and then a 0.22μ filter and then concentrated ~25-fold and buffer exchanged into PBS using tangential flow filtration (TFF) through a Minimate TFF Capsule 500 k Omega Membrane (PALL).

Removal of endotoxin was achieved with ethanol precipitation followed by precipitation with Triton X-100. Ethanol was added to the retentate to 30% and the material was allowed to precipitate overnight at room temperature. The precipitate was removed by centrifugation and filtration through a 0.22p filter. PBS was added to the remaining filtered supernatant to reduce the ethanol concentration to 25% and the bulk material was again processed through TFF using the Minimate TFF Capsule 500 k Omega Membrane. The material was diafiltered with 4 times the volume of PBS+25% Ethanol followed by 4 times the volume of PBS. The volume of the retentate was subsequently reduced by 2-fold to approximately 1/50 of the original culture volume. The retentate was cooled to 4° C. and Triton X-114 was added to 0.33-0.67% (v/v). The material was slowly warmed to ~37° C. while centrifuged to remove the precipitate. The final material was concentrated and washed with PBS using a Macrosep ADV 100 KD filtration device to a volume ~1/100 of the original culture volume.

ATHR-M1 was biochemically characterized. The particle count was established using the NanoSight NS300 Instrument (Malvern Panalytical) with nanoparticle tracking analysis (NTA) software to establish the size and count of bionanoparticles. Dot blots, Western blots and sandwich ELISAs with antibodies against the S-RBD were used to establish expression of the S-RBD on the surface of the phage. The functionality of the displayed S-RBD fragment was demonstrated by its binding to recombinant ACE2 protein by ELISA.

The immunogenicity of ATHR-M1 was established by vaccination of balb/c mice. Mice were vaccinated subcutaneously with three doses of ATHR-M1 of $\sim 1\times 10^9$ particles per dose in phosphate buffered saline. The 3 doses were delivered at two-week intervals. Control animals received a similar dose of wild-type phage A that do not display any added protein fragment. A final (fourth) higher boost of ATHR-M1 of $1\times 10^{11}$ particles was delivered ~3 weeks after the third dose. Mice were sacrificed 7 days after the final boost; spleens were harvested to prepare splenocytes and serum was collected for the measure of antibodies.

Serum antibody levels were determined by a standard ELISA assay in which recombinant S-RBD was used as the capture agent and detection used antibodies labeled with horse-radish peroxidase (HRP) with specificity towards murine IgG, IgM and IgA. Results are shown in Table 1, below and FIG. 3.

TABLE 1

| Control Animal No. | Serum antibody level (ng/ml) | Vaccinated Animal No. | Serum antibody level (ng/ml) |
|---|---|---|---|
| 13 | 0 | 1 | 24.25 |
| 14 | 0.1 | 2 | 25.5 |
| 15 | 0 | 3 | 23.25 |
| 16 | 0.56 | 4 | 63 |
| 17 | 0 | 5 | 42.8 |
| 18 | 1.65 | 6 | 34.6 |
| Mean ± sd | 0.38 ± 0.66 | Mean ± sd | 35.9 ± 15.1 |

As can be seen in Table 1 and FIG. 3, vaccinated animals had significantly higher levels of anti-S-RBD antibodies in their serum as compared to control mice.

B-cell responses were further characterized in isolated mouse splenocytes by ELISPOT again using recombinant S-RBD as the capture reagent and anti-mouse IgG and IgM antibodies for detection. Splenocytes were cultured for 4 days with either no added stimulatory agent or with ATHR-M1 and recombinant S-RBD as the stimulatory reagent prior to the ELISPOT assay. Results are shown in Table 2, below, and FIG. 4.

TABLE 2

| Control No. | No further stim. agent | SRBD + ATHR-M1 | Sample No. | No further stim. agent | SRBD + ATHR-M1 |
|---|---|---|---|---|---|
| 13 | 6 | 33 | 13 | 17 | 61 |
| 14 | 4 | 38 | 14 | 14 | 45 |
| 15 | 7 | 53 | 15 | 24 | 50 |
| Mean ± sd | 6 ± 2 | 41 ± 10 | Mean ± sd | 18 ± 5 | 53 ± 8 |

As can be seen, even without further stimulation splenocytes isolated from ATHR-M1 vaccinated mice had 3-times the number of B-cells producing antibodies against S-RBD.

Figure 5:
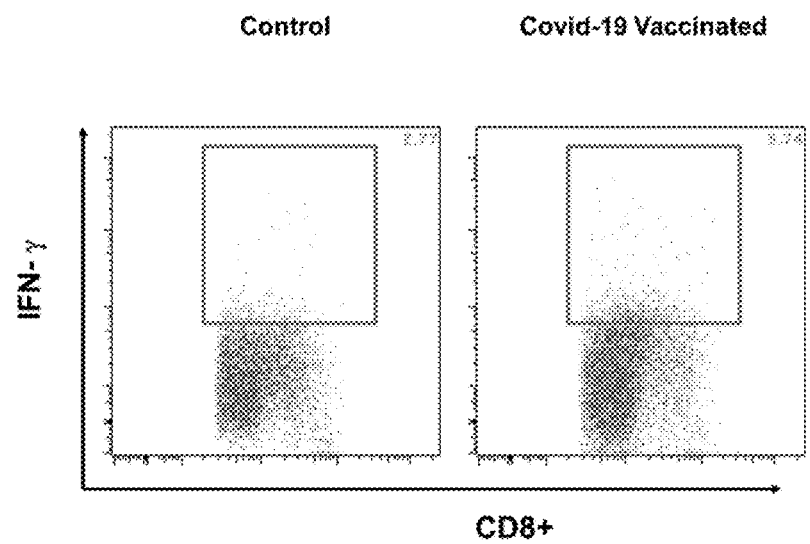
FIG. 5 compares the surface expression of CD8 on T-cells of subjects immunized with a vaccine comprising ATHR-M1 as described compared to control subjects.
Figure 6:
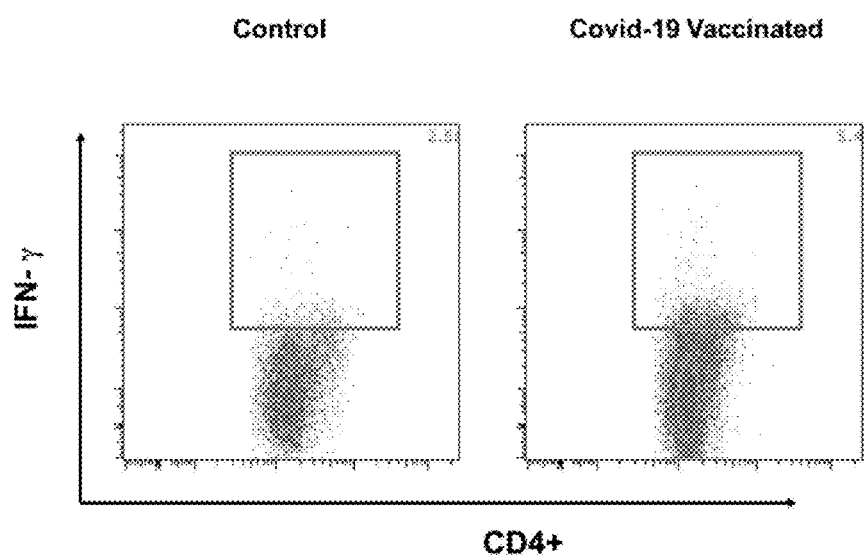
FIG. 6 compares the surface expression of CD4 on T-cells of subjects immunized with a vaccine comprising ATHR-M1 as described compared to control subjects.

T-cell responses were explored using flow cytometry assays. Splenocytes were treated as above and cells individual IFNγ producing T-cells were identified by surface expression of CD8 or CD4. As illustrated in FIG. 5 and FIG. 6, a two-fold increase in the percentage of activated cytotoxic T-cells (CD8+) and helper T-cells (CD4+) was identified in ATHR-M1 vaccinated mice vs. control vaccinated mice.

In another in vivo study, the immunogenicity of ATHR-M1 was established by vaccination of balb/c mice. Mice were vaccinated subcutaneously with two doses of ATHR-M1 of ~5×10$^{10}$ particles per dose in phosphate buffered saline. The 2 doses were delivered at two-week intervals on Day 0 and Day 14 of the experiment. Control animals received a similar dose of wild-type phage λ that do not display any added protein fragment. Serum was collected from the mice every 7 days, on Days 0, 7, 14, 21, 28, 35 and 42. Initially, there was a group of 7 mice, but 3 mice were sacrificed on Day 14, 3 on Day 28 and one on Day 42.

Figure 7:
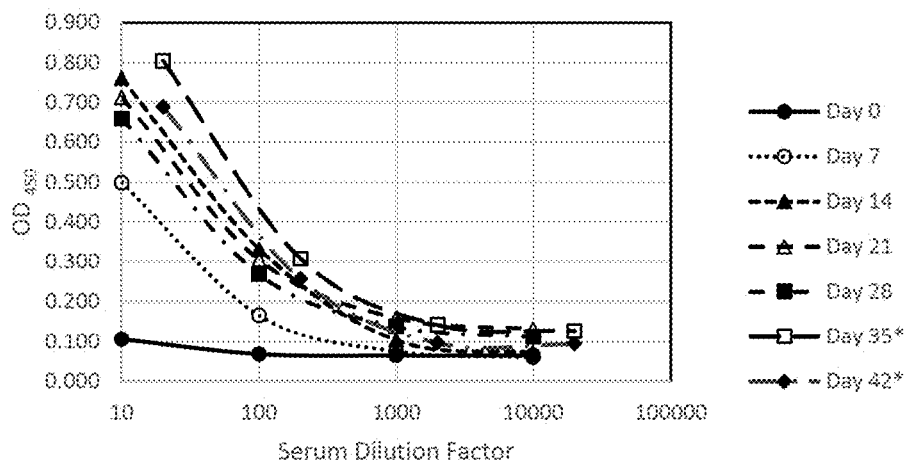
FIG. 7 graphically illustrates serum antibody levels of subjects immunized with a vaccine comprising ATHR-M1 as described over time by use of an ELISA assay in which recombinant S-RBD was used as the capture agent.
Figure 8:
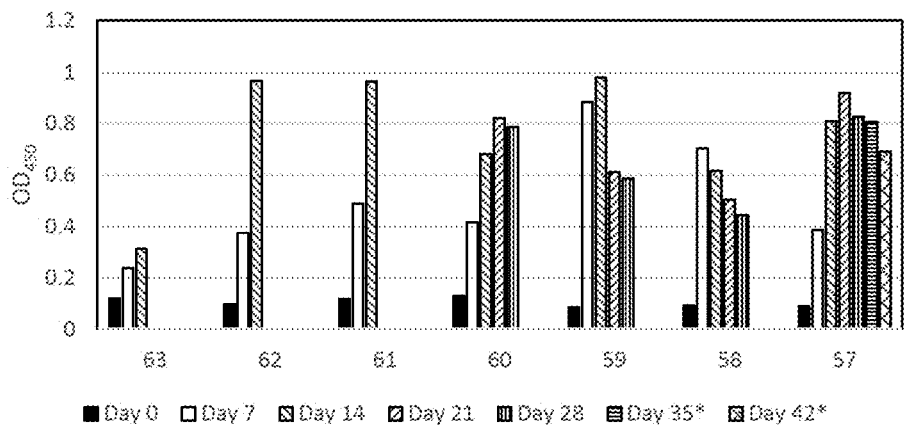
FIG. 8 graphically illustrates serum antibody levels of subjects immunized with a vaccine comprising ATHR-M1 as described over time by use of antibodies labeled with horse-radish peroxidase (HRP) with specificity towards murine IgG, IgM and IgA.

Serum antibody levels were determined by a standard ELISA assay in which recombinant S-RBD was used as the capture agent and detection used antibodies labeled with horse-radish peroxidase (HRP) with specificity towards murine IgG, IgM and IgA. Results are shown in FIG. 7 and FIG. 8. Immunogenicity was noted in all 7 animals in the cohort and anti-S-RBD antibodies could be detected in serum as early as Day 7 and peaked at Day 14, prior to the second vaccination (boost). High levels of antibodies remained through the end of the experiment at Day 42 in the last remaining animal.

Example 2

An engineered bacteriophage was formed (ATHR-M2) that included multiple different fragments of structural proteins from SARS-CoV-2 displayed on the surface of the phage.

Phage lambda were engineered as described above in Example 1, however in this instance multiple gpD fusion proteins were expressed simultaneously within the bacterium during phage expression. Five separate fragments from the SARS-CoV-2 spike protein (accession numbers previously provided) were expressed, specifically S1a (amino acid residues 16-318), S1b (amino acid residues 319-529), S1c (amino acid residues 530-690), S2a (amino acid residues 691-950) and S2b (amino acid residues 951-1213). Two fragments covering the sequence of the SARS-CoV-2 nucleocapsid protein were also incorporated: N1 (amino acid residues 1-299) and N2 (amino acid residues 300-419).

A nucleotide sequence encoding a fusion protein consisting of gpD, a linker and S1a optimized for codon usage in *E. coli* K12 (SEQ ID NO: 5) was cloned in the expression vector pACYCDuet-1 (Novagen) in the first multi-cloning site at the restriction site for NcoI.

```
                                              SEQ ID NO: 5
  1 MTSKETFTHYQPQGNSDPAHTATAPGGLSAKAPAMTPLMLDTSSRKLVAW    50

51 DGTTDGAAVGILAVAADQTSTTLTFYKSGTFRYEDVLWPEAASDETKKRT   100

101 AFAGTAISIVGGSGPVGPGGSGASVNLTTRTQLPPAYTNSFTRGVYYPDK   150

151 VFRSSVLHSTQDLFLPFFSNVTWFHAIHVSGTNGTKRFDNPVLPFNDGVY   200

201 FASTEKSNIIRGWIFGTTLDSKTQSLLIVNNATNVVIKVCEFQFCNDPFL   250

251 GVYYHKNNKSWMESEFRVYSSANNCTFEYVSQPFLMDLEGKQGNFKNLRE   300

301 FVFKNIDGYFKIYSKHTPINLVRDLPQGFSALEPLVDLPIGINITRFQTL   350

351 LALHRSYLTPGDSSSGWTAGAAAYYVGYLQPRTFLLKYNENGTITDAVDC   400

401 ALDPLSETKCTLKSFTVEKGIYQTSNF                         427
```

A nucleotide sequence encoding a fusion protein consisting of gpD, a linker and S1b optimized for codon usage in *E. coli* K12 (SEQ ID NO: 1, Example 1) was cloned into the expression vector pACYCDuet-1 (Novagen) in the second multi-cloning site at the restriction site for NdeI.

A nucleotide sequence encoding a fusion protein consisting of gpD, a linker and S1c optimized for codon usage in *E. coli* K12 (SEQ ID NO: 6) was cloned into the expression vector pCOLADuet-1 (Novagen) in the first multi-cloning site at the restriction site for NcoI.

```
                                              SEQ ID NO: 6
  1 MTSKETFTHYQPQGNSDPAHTATAPGGLSAKAPAMTPLMLDTSSRKLVAW    50

51 DGTTDGAAVGILAVAADQTSTTLTFYKSGTFRYEDVLWPEAASDETKKRT   100

101 AFAGTAISIVGGSGPVGPGGSGASSTNLVKNKCVNFNFNGLTGTGVLTES   150

151 NKKFLPFQQFGRDIADTTDAVRDPQTLEILDITPCSFGGVSVITPGTNTS   200

201 NQVAVLYQDVNCTEVPVAIHADQLTPTWRVYSTGSNVFQTRAGCLIGAEH   250

251 VNNSYECDIPIGAGICASYQTQTNSPRRARSVASQ                 335
```

A nucleotide sequence encoding a fusion protein consisting of gpD, a linker and S2a optimized for codon usage in *E. coli* K12 (SEQ ID NO: 7) was cloned into the expression vector pETDuet-1 (Novagen) in the first multi-cloning site at the restriction site for NcoI.

```
                                              SEQ ID NO: 7
  1 MTSKETFTHYQPQGNSDPAHTATAPGGLSAKAPAMTPLMLDTSSRKLVAW    50

51 DGTTDGAAVGILAVAADQTSTTLTFYKSGTFRYEDVLWPEAASDETKKRT   100

101 AFAGTAISIVGGSGPVGPGGSGASSIIAYTMSLGAENSVAYSNNSIAIPT   150

151 NFTISVTTEILPVSMTKTSVDCTMYICGDSTECSNLLLQYGSFCTQLNRA   200

201 LTGIAVEQDKNTQEVFAQVKQIYKTPPIKDFGGFNFSQILPDPSKPSKRS   250

251 FIEDLLFNKVTLADAGFIKQYGDCLGDIAARDLICAQKFNGLTVLPPLLT   300

301 DEMIAQYTSALLAGTITSGWTFGAGAALQIPFAMQMAYRENGIGVTQNVL   350

351 YENQKLIANQFNSAIGKIQDSLSSTASALGKLQD                   384
```

A nucleotide sequence encoding a fusion protein consisting of gpD, a linker and S2b optimized for codon usage in *E. coli* K12 (SEQ ID NO: 8) was cloned into the expression vector pETDuet-1 (Novagen) in the second multi-cloning site at the restriction site for NdeI.

```
                                              SEQ ID NO: 8
  1 MTSKETFTHYQPQGNSDPAHTATAPGGLSAKAPAMTPLMLDTSSRKLVAW    50

51 DGTTDGAAVGILAVAADQTSTTLTFYKSGTFRYEDVLWPEAASDETKKRT   100

101 AFAGTAISIVGGSGPVGPGGSGASVVNQNAQALNTLVKQLSSNFGAISSV   150

151 LNDILSRLDKVEAEVQIDRLITGRLQSLQTYVTQQLIRAAEIRASANLAA   200

201 TKMSECVLGQSKRVDFCGKGYHLMSFPQSAPHGVVFLHVTYVPAQEKNFT   250

251 TAPAICHDGKAHFPREGVFVSNGTHWFVTQRNFYEPQIITTDNTFVSGNC   300

301 DVVIGIVNNTVYDPLQPELDSFKEELDKYFKNHTSPDVDLGDISGINASV   350

351 VNIQKEIDRLNEVAKNLNESLIDLQELGKYEQYIKWP                387
```

A nucleotide sequence encoding a fusion protein consisting of gpD, a linker and Na optimized for codon usage in *E. coli* K12 (SEQ ID NO: 9) was cloned into the expression vector pCDFDuet-1 (Novagen) in the first multi-cloning site at the restriction site for NcoI.

```
                                              SEQ ID NO: 9
  1 MTSKETFTHYQPQGNSDPAHTATAPGGLSAKAPAMTPLMLDTSSRKLVAW    50

51 DGTTDGAAVGILAVAADQTSTTLTFYKSGTFRYEDVLWPEAASDETKKRT   100

101 AFAGTAISIVGGSGPVGPGGSGASMSDNGPQNQRNAPRITFGGPSDSTGS   150

151 NQNGERSGARSKQRRPQGLPNNTASWFTALTQHGKEDLKFPRGQGVPINT   200

201 NSSPDDQIGYYRRATRRIRGGDGKMKDLSPRWYFYYLGTGPEAGLPYGAN   250

251 KDGIIWVATEGALNTPKDHIGTRNPANNAAIVLQLPQGTTLPKGFYAEGS   300

301 RGGSQASSRSSSRSRNSSRNSTPGSSRGTSPARMAGNGGDAALALLLLDR   350

351 LNQLESKMSGKGQQQQGQTVTKKSAAEASKKPRQKRTATKAYNVTQAFGR   400

401 RGPEQTQGNFGDQELIRQGTDYK                              424
```

A nucleotide sequence encoding a fusion protein consisting of gpD, a linker and S2b optimized for codon usage in *E. coli* K12 (SEQ ID NO: 10) was cloned into the expression vector pCDFDuet-1 (Novagen) in the second multi-cloning site at the restriction site for NdeI.

```
                                                         SEQ ID NO: 10
  1 MTSKETFTHYQPQGNSDPAHTATAPGGLSAKAPAMTPLMLDTSSRKLVAW      50

51 DGTTDGAAVGILAVAADQTSTTLTFYKSGTFRYEDVLWPEAASDETKKRT     100

101 AFAGTAISIVGGSGPVGPGGSGASHWPQIAQFAPSASAFFGMSRIGMEVT     150

151 PSGTWLTYTGAIKLDDKDPNFKDQVILLNKHIDAYKTFPPTEPKKDKKKK     200

201 ADETQALPQRQKKQQTVTLLPAADLDDFSKQLQQSMSSADSTQA           244
```

All four expression vectors were co-transfected into *E. coli* BL21 (DE3) and the *E. coli* were selected on chloramphenicol, kanamycin, ampicillin and streptomycin containing medium. Phage expression, isolation, endotoxin removal and characterization were as above in Example 1. These phage were designated as ATHR-M2.

Figure 9:
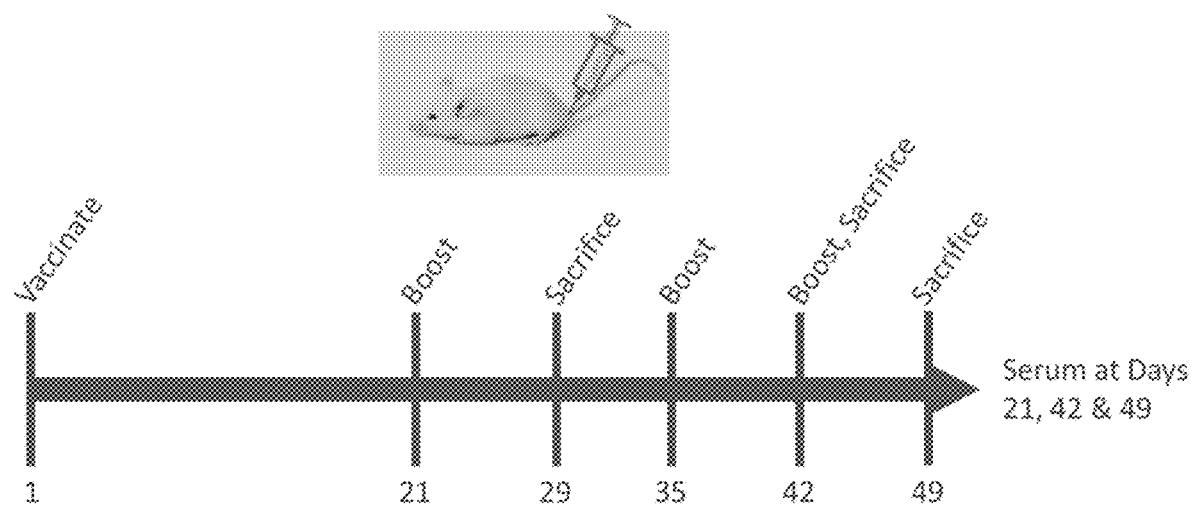
FIG. 9 illustrates an immunogenicity study as described further herein.

FIG. 9 generally shows the immunogenicity studies carried out with ATHR-M2. Briefly, Balb/c mice were vaccinated on Day 1 of the study with nine mice per group at a dose of $5 \times 10^{10}$ phage. Animals in a control group received a similar dose of wild-type phage λ that do not display any added protein fragment.

Group 1 was sacrificed on Day 29. Group 2 was sacrificed on Day 42. Group 3 was sacrificed on Day 49. One or two animals from the control group were sacrificed at each time point.

Figure 10:
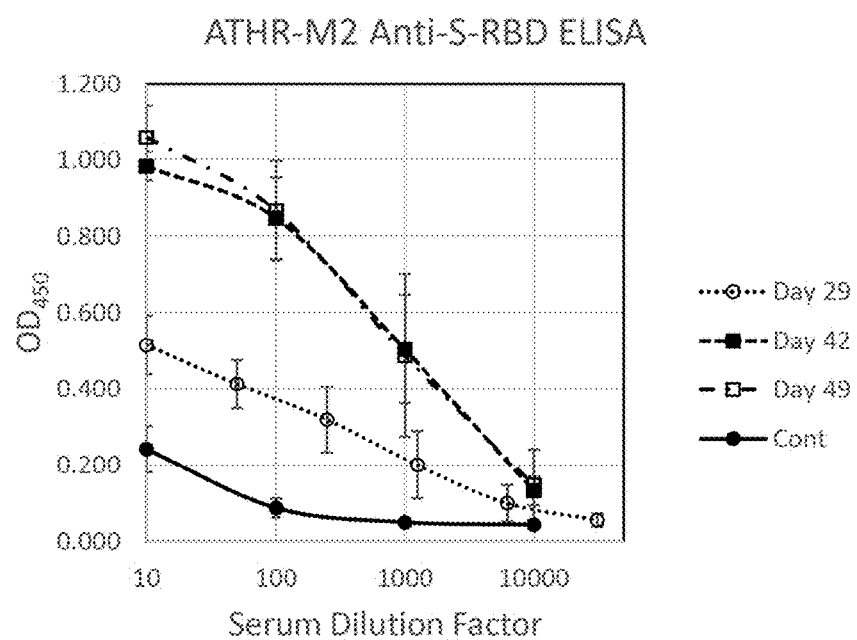
FIG. 10 graphically compares the total serum antibody levels of subjects immunized with a vaccine comprising ATHR-M2 as described compared to control subjects.

FIG. 10 illustrates serum antibody levels obtained for anti-COVID-19 S-RBD. Recombinant S-RBD was used as the capture agent and detection used antibodies labeled with horse-radish peroxidase (HRP) with specificity towards murine IgG, IgM and IgA. Serum was titered and the averaged signal from the vaccinated mice was determined (n=9). All mice in each group responded. As shown, high titers of anti-S-RBD antibodies were identified after a single vaccination and boost. Titers continued to increase after a second boost and subsequently stabilized.

Figure 11:
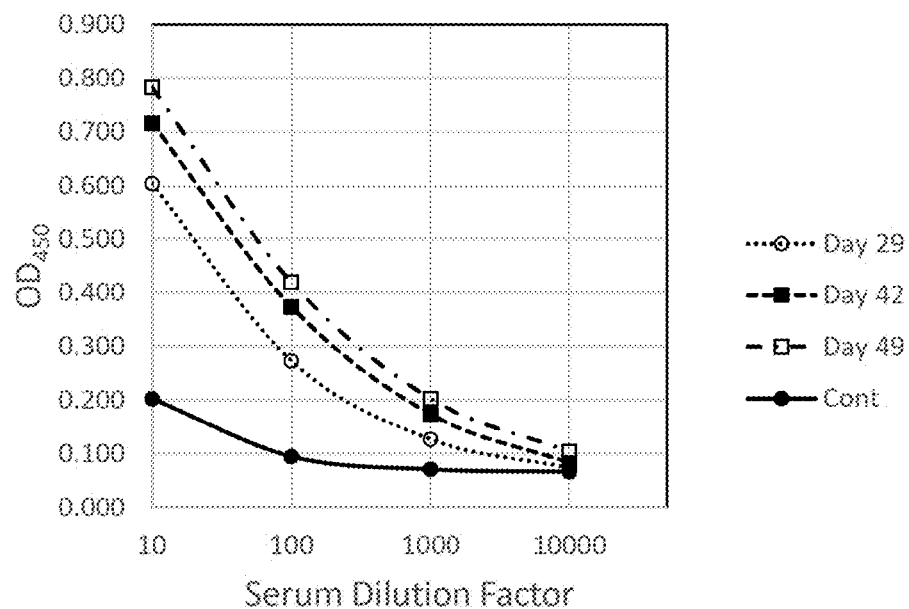
FIG. 11 illustrates serum antibody levels obtained for an antibody against one antigen of a multi-valent vaccine comprising ATHR-M2 as described herein.

FIG. 11 illustrates serum antibody levels obtained for anti-COVID-19 S1. Recombinant S1 was used as the capture agent and detection used antibodies labeled with horse-radish peroxidase (HRP) with specificity towards murine IgG, IgM and IgA. Serum was titered and the averaged signal from the vaccinated mice was determined (n=9). All mice in each group responded. As shown, high titers of anti-S1 antibodies were identified after a single vaccination and boost.

Figure 12:
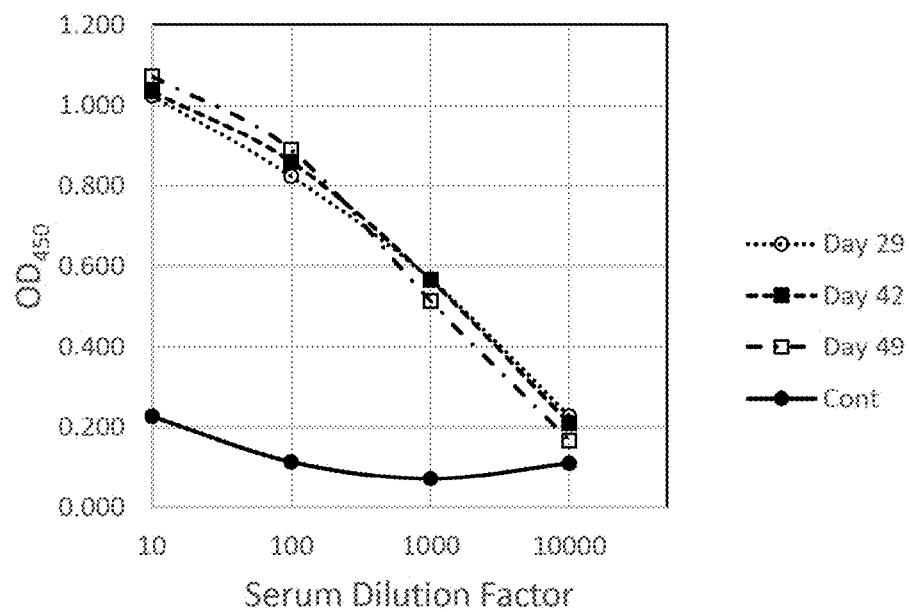
FIG. 12 illustrates serum antibody levels obtained for an antibody against another antigen of the multi-valent vaccine comprising ATHR-M2.

FIG. 12 illustrates serum antibody levels obtained for anti-COVID-19 S2. Recombinant S2 was used as the capture agent and detection used antibodies labeled with horse-radish peroxidase (HRP) with specificity towards murine IgG, IgM and IgA. Serum was titered and the averaged signal from the vaccinated mice was determined (n=9). All mice in each group responded. As shown, extremely high titers of anti-S2 antibodies were identified after a single vaccination and boost. By day 29, these antibody levels achieved the maximum level.

Figure 13:
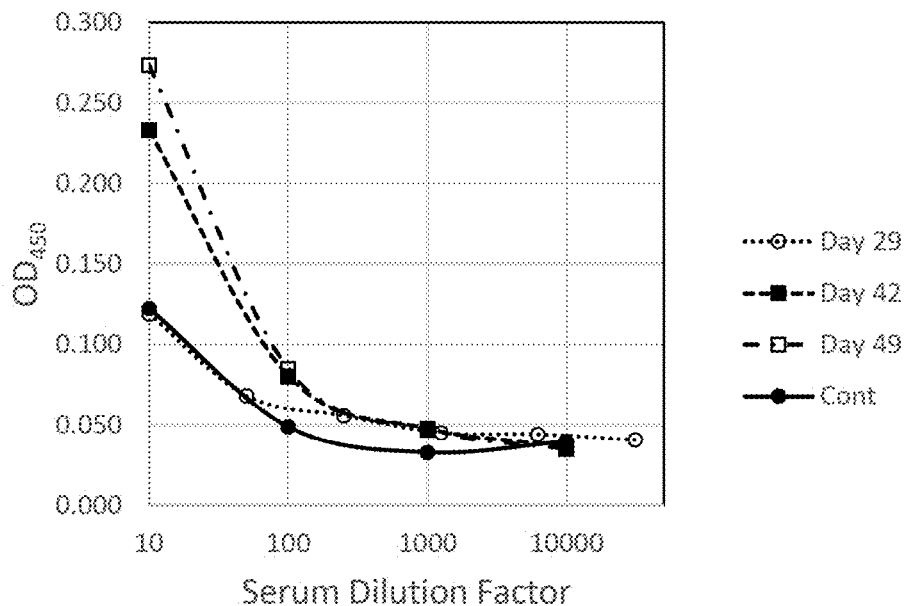
FIG. 13 illustrates serum antibody levels obtained for an antibody against another antigen of the multi-valent vaccine comprising ATHR-M2.
Figure 14:
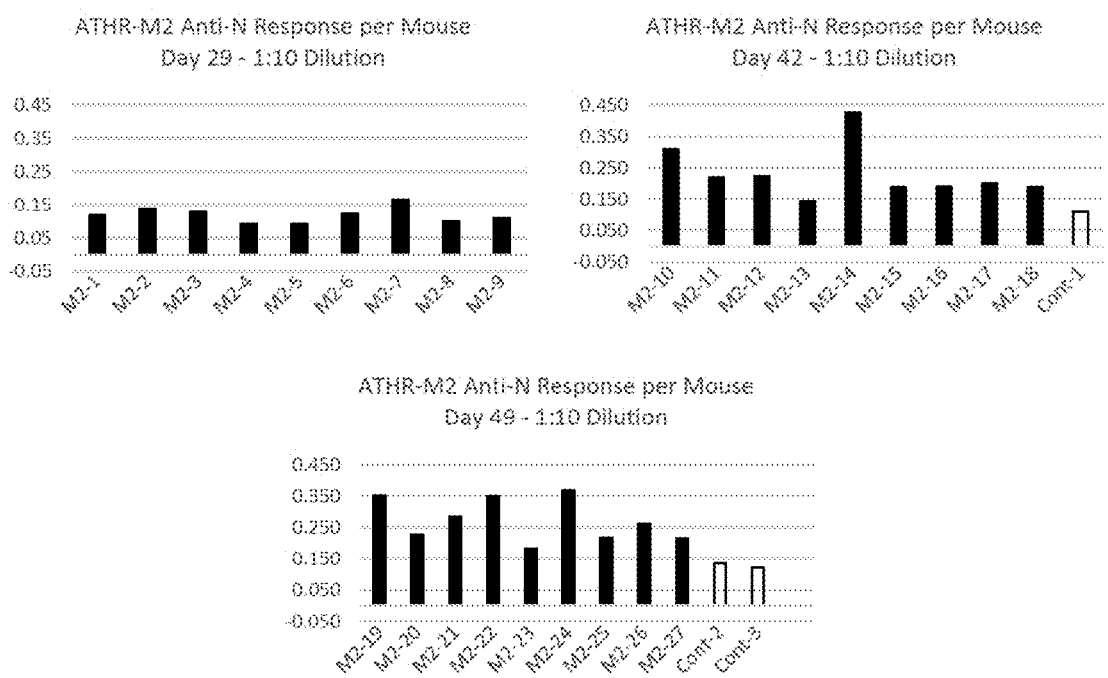
FIG. 14 illustrates the variability in response by individual subjects to one of the multiple antigens of the multi-valent vaccine comprising ATHR-M2.

FIG. 13 illustrates serum antibody levels obtained for anti-COVID-19 N, both as a whole and as a response by subject at each time point as indicated. Recombinant N was used as the capture agent and detection used antibodies labeled with horse-radish peroxidase (HRP) with specificity towards murine IgG, IgM and IgA. Serum was titered and the averaged signal from the vaccinated mice was determined (n=9). For this antigen, there was much more variability in response by individual mice as compared to other antigens of the vaccine (FIG. 14). Antibody responses against the nucleocapsid protein were less prevalent, although some animals did produce these antibodies.

Figure 15:
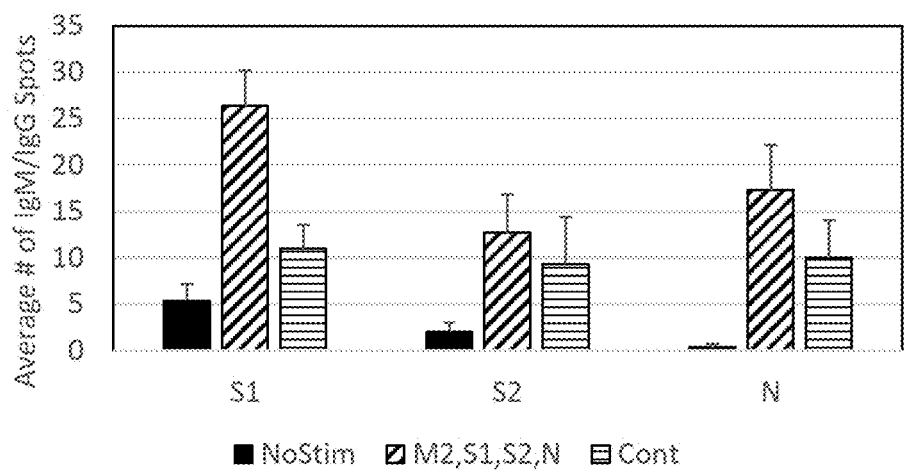
FIG. 15 graphically illustrates the B-cell response of subjects to the multi-valent vaccine comprising ATHR-M2.
Figure 16:
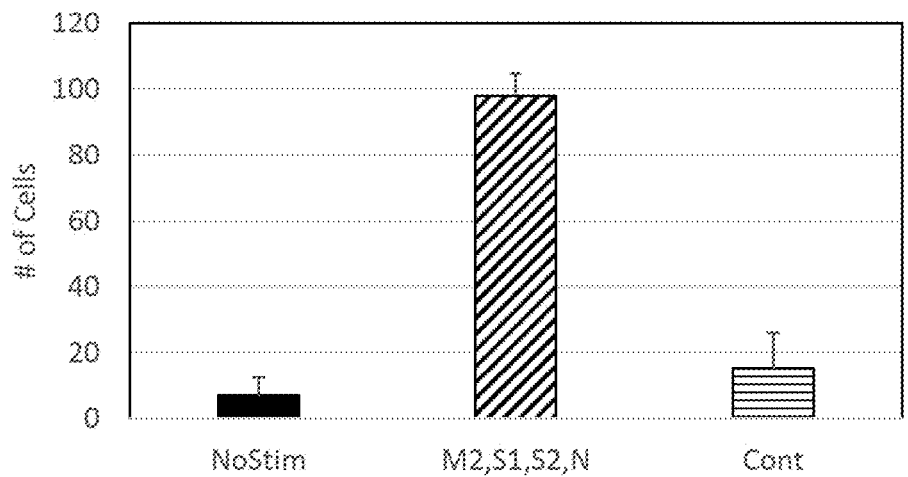
FIG. 16 graphically illustrates the T-cell response of subjects to the multi-valent vaccine comprising ATHR-M2.

B-cell and T-cell responses were determined by ELISPOT. Briefly, ELISPOT membranes were coated with a protein (i.e., S1, S2, N). Splenocytes harvested at Day 29 were cultured for 4 days prior to the ELISPOT procedure with either no stimulus (left bars), a mix of ATHR-M2 and recombinant proteins, or the control phage. As indicated in FIG. 15, B-cells that produce IgG or IgM antibodies against S1, S2, and N were found in the spleens of vaccinated mice after a single vaccination and boost. As indicated in FIG. 16, T-cells were activated by the vaccine and recombinant proteins, but much less so by the control phage.

Figure 17:
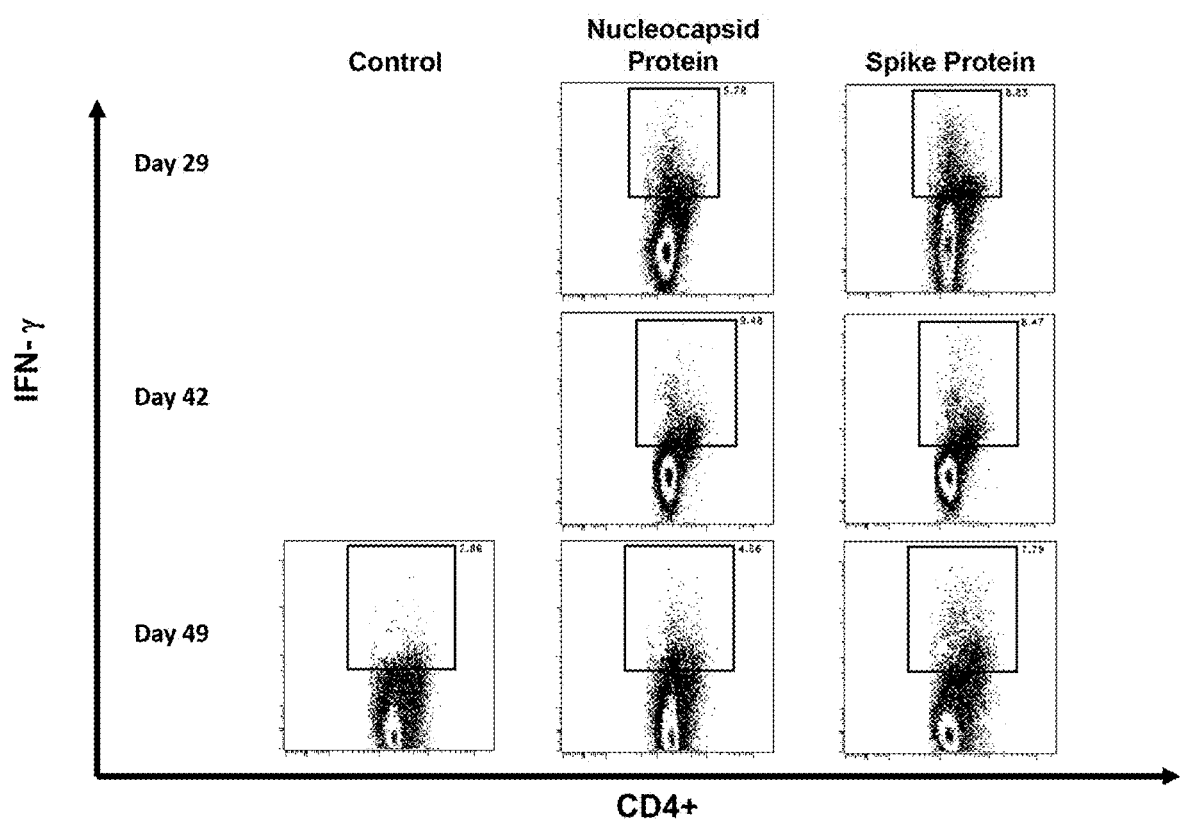
FIG. 17 presents CD4+ T-cell data responses as measured by flow cytometry of subjects to the multi-valent vaccine comprising ATHR-M2.
Figure 18:
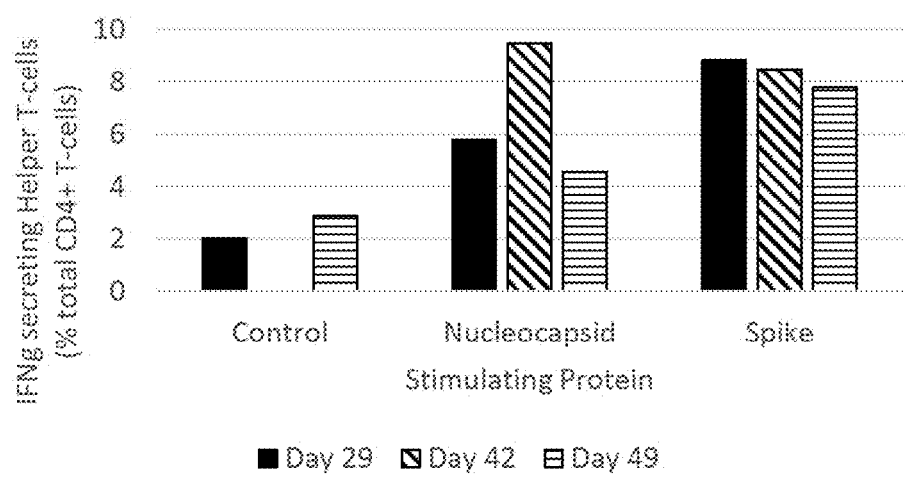
FIG. 18 graphically presents CD4+ T-cell data responses as measured by flow cytometry of subjects to the multi-valent vaccine comprising ATHR-M2.

CD4+ T-cell data responses as measured by flow cytometry are presented in FIG. 17 and FIG. 18. As shown, helper T-cells specifically activated by either the spike or nucleocapsid proteins were found in the spleens of the vaccinated mice as early as Day 29 following initial immunization.

Figure 19:
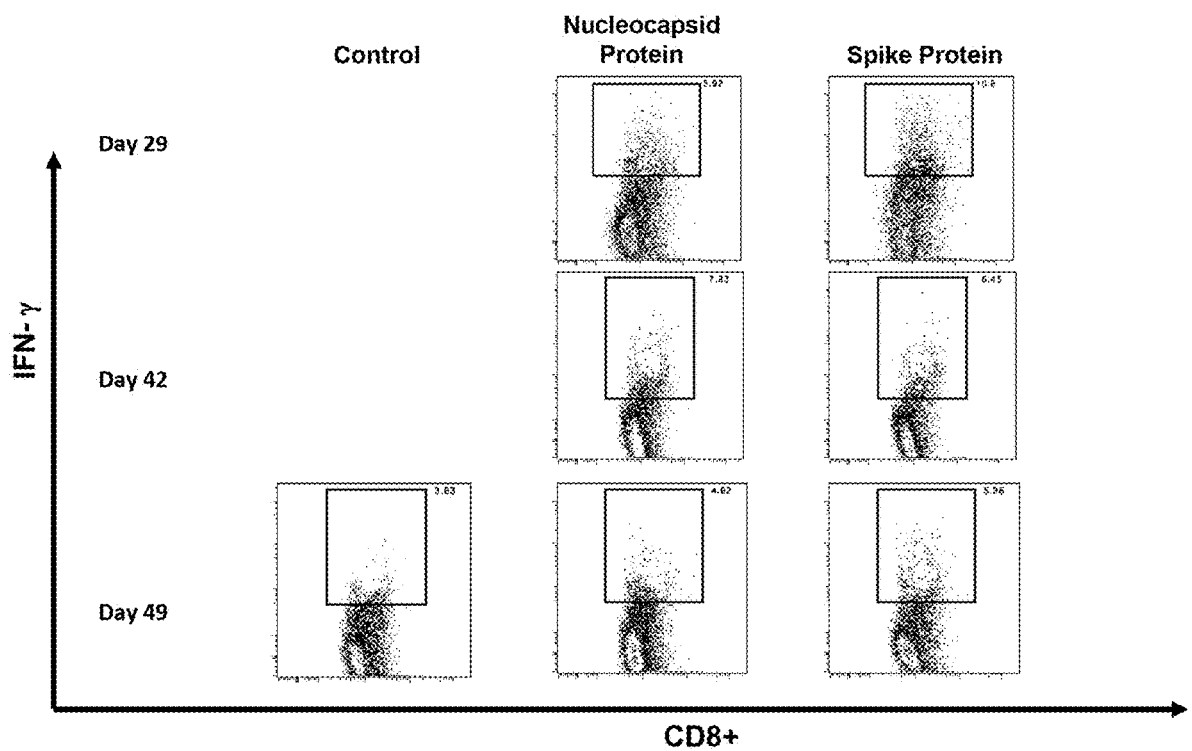
FIG. 19 presents CD8+ T-cell data responses as measured by flow cytometry of subjects to the multi-valent vaccine comprising ATHR-M2.
Figure 20:
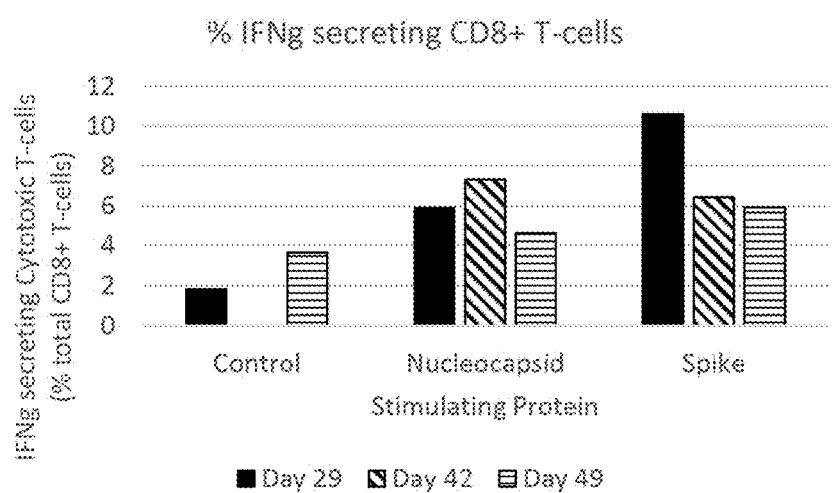
FIG. 20 graphically presents CD8+ T-cell data responses as measured by flow cytometry of subjects to the multi-valent vaccine comprising ATHR-M2.

CD8+ T-cell data responses as measured by flow cytometry are presented in FIG. 19 and FIG. 20. As shown, helper T-cells specifically activated by either the spike or nucleocapsid proteins were found in the spleens of the vaccinated mice as early as Day 29 following initial immunization.

Example 3

In this example, protein fragments from multiple viral strains were displayed on the same multivalent phage. Specifically, the expression of five of the S-RBD sequences from different strains of coronavirus were presented on the same phage using the process outlined in Example 1. The five nucleotide sequences encoding the fusion proteins each encoded gpD, a linker, and a protein fragment sequence from a strain of the coronavirus (accession numbers for the various proteins provided previously). The protein fragments and nucleotide sequences encoding the fusion proteins were as follows:

SARS-CoV-2 S-protein RBD (amino acid residues 319-529)—SEQ ID NO: 1 as described in Example 1.

SARS-CoV-1 S-protein RBD (amino acid residues 306-515)

```
                                           SEQ ID NO: 11
  1 MTSKETFTHYQPQGNSDPAHTATAPGGLSAKAPAMTPLMLDTSSRKLVAW   50

51 DGTTDGAAVGILAVAADQTSTTLTFYKSGTFRYEDVLWPEAASDETKKRT  100

101 AFAGTAISIVGGSGPVGPGGSGASRVVPSGDVVREPNITNLCPFGEVFNA  150

151 TKFPSVYAWERKKISNCVADYSVLYNSTFFSTFKCYGVSATKLNDLCFSN  200

201 VYADSFVVKGDDVRQIAPGQTGVIADYNYKLPDDFMGCVLAWNTRNIDAT  250

251 STGNYNYKYRYLRHGKLRPFERDISNVPFSPDGKPCTPPALNCYWPLNDY  300

301 GFYTTTGIGYQPYRVVVLSFELLNAPATVCGPKL                 334
```

MERS S-protein RBD (amino acid residues 364-594)

```
                                           SEQ ID NO: 12
  1 MTSKETFTHYQPQGNSDPAHTATAPGGLSAKAPAMTPLMLDTSSRKLVAW   50

51 DGTTDGAAVGILAVAADQTSTTLTFYKSGTFRYEDVLWPEAASDETKKRT  100

101 AFAGTAISIVGGSGPVGPGGSGASEAKPSGSVVEQAEGVECDFSPLLSGT  150

151 PPQVYNFKRLVFTNCNYNLTKLLSLESVNDFTCSQISPAAIASNCYSSLI  200

201 LDYFSYPLSMKSDLSVSSAGPISQFNYKQSFSNPTCLILATVPHNLTTIT  250

251 KPLKYSYINKCSRLLSDDRTEVPQLVNANQYSPCVSIVPSTVWEDGDYYR  300

301 KQLSPLEGGGWLVASGSTVAMTEQLQMGFGITVQYGTDTNSVCPKLEFAN  350

351 DT                                                 352
```

NL63 S-protein RBD (amino acid residues 465-618)

```
                                           SEQ ID NO: 13
  1 MTSKETFTHYQPQGNSDPAHTATAPGGLSAKAPAMTPLMLDTSSRKLVAW   50

51 DGTTDGAAVGILAVAADQTSTTLTFYKSGTFRYEDVLWPEAASDETKKRT  100

101 AFAGTAISIVGGSGPVGPGGSGASDDNVLPETYVALPIYYQHTDINFTAT  150

151 ASFGGSCYVCKPHQVNISLNGNTSVCVRTSHFSIRYIYNRVKSGSPGDSS  200

201 WHIYLKSGTCPFSFSKLNNFQKFKTICFSTVEVPGSCNFPLEATWHYTSY  250

251 TIVGALYVTWSEGNSITGVPYPVSGIRE                       278
```

229E S-protein RBD (e.g., amino acid residues 271-435)

```
                                           SEQ ID NO: 14
  1 MTSKETFTHYQPQGNSDPAHTATAPGGLSAKAPAMTPLMLDTSSRKLVAW   50

51 DGTTDGAAVGILAVAADQTSTTLTFYKSGTFRYEDVLWPEAASDETKKRT  100

101 AFAGTAISIVGGSGPVGPGGSGASQPVELPVSIVSLPVYHKHTFIVLYVN  150

151 FEHQRGPGKCYNCRPAVINITLANFNETKGPLCVDTSHFTTQFVDNVKLA  200

201 RWSASINTGNCPFSEGKVINFVKFGSVCFSLKYIPGGCAMPIMANLVNHK  250

251 SHNIGSLYVSWSDGDVITGVPKPVEGVSS                      279
```

The DNA encoding the gpD-linker-SARS-CoV-1 S-protein RBD (SEQ ID NO: 11) was cloned into the expression vector pACYCDuet-1 (Novagen) in the first multi-cloning site at the restriction site for NcoI and the DNA encoding the gpD-linker-SARS-CoV-2 S-protein RBD (SEQ ID NO: 1) was cloned into the same vector in the second multi-cloning site at the restriction site for NdeI.

The DNA encoding the gpD-linker-MERS S-protein RBD (SEQ ID NO: 12) was cloned into the expression vector pCOLADuet-1 (Novagen) in the first multi-cloning site at the restriction site for NcoI.

The DNA encoding the gpD-linker-NL63 S-protein RBD (SEQ ID NO: 13) was cloned into the expression vector pETDuet-1 (Novagen) in the first multi-cloning site at the restriction site for NcoI and the DNA encoding the gpD-linker-229E S-protein RBD (SEQ ID NO: 14) was cloned into the same vector in the second multi-cloning site at the restriction site for NdeI.

The resulting multivalent bacteriophage (referred to herein as ATHR-M3) could elicit an immune response to prevent infection by any and all of the coronavirus strains known to infect humans. Moreover, such a vaccine may give even broader immunity against future coronavirus strains, given that they are likely to be derivatives/mutants of the know strains.

Figure 21:
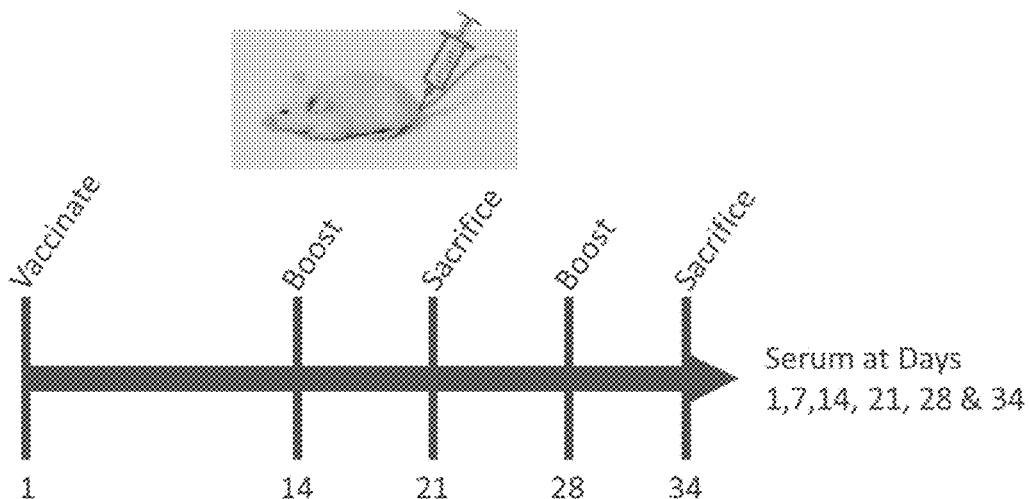
FIG. 21 illustrates another immunogenicity study as described further herein.

FIG. 21 generally shows the immunogenicity studies carried out with ATHR-M3. Briefly, Balb/c mice were vaccinated on Day 1 of the study with seven mice per group. Three doses were investigated:

Low Dose=$1\times10^{10}$ particles per dose.
Medium Dose=$5\times10^{10}$ particles per dose.
High Dose=$1\times10^{11}$ particles per dose.

Serum was sampled every 7 days until sacrifice. 3 mice in each group were sacrificed on Day 21. The remaining 4 mice in each group were sacrificed on Day 34.

Figure 22:
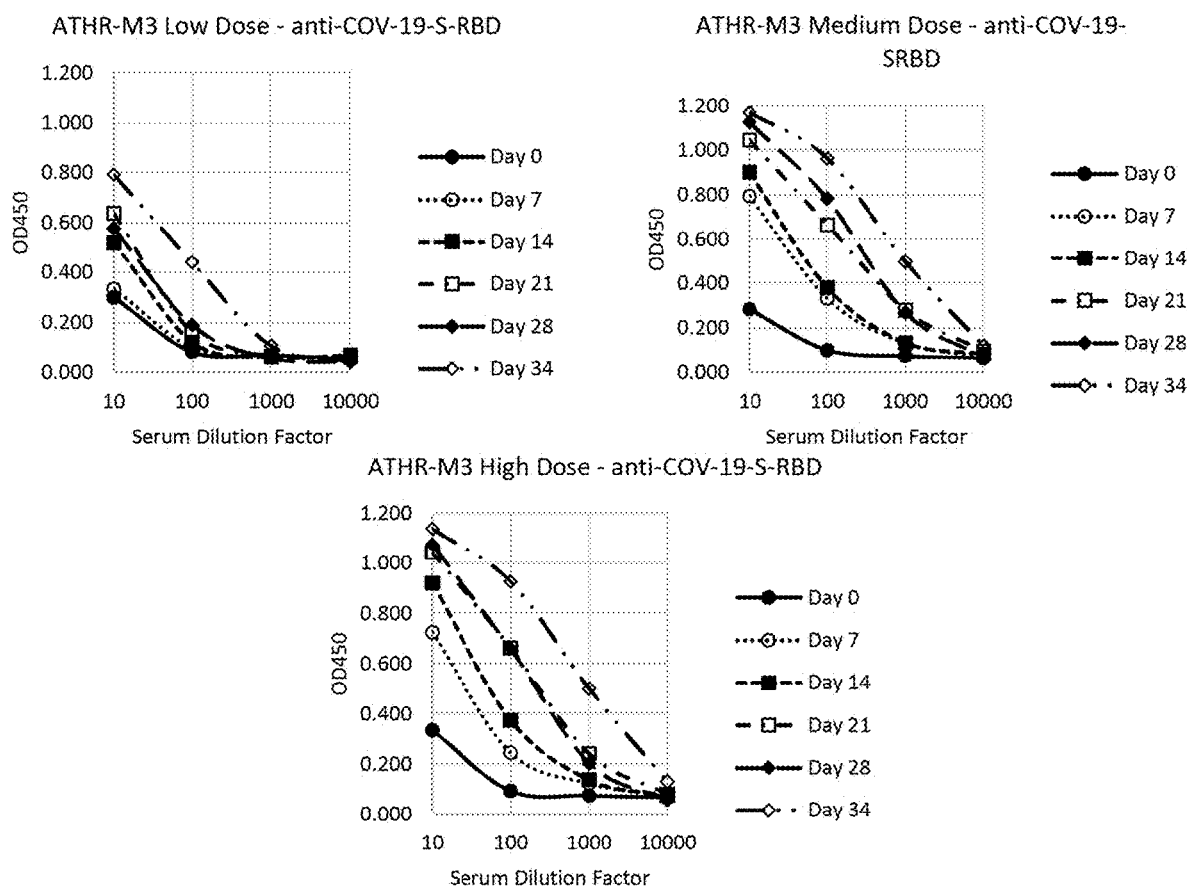
FIG. 22 illustrates serum antibody levels obtained for an antibody against one antigen of a multi-valent vaccine comprising ATHR-M3 as described herein.
Figure 23:
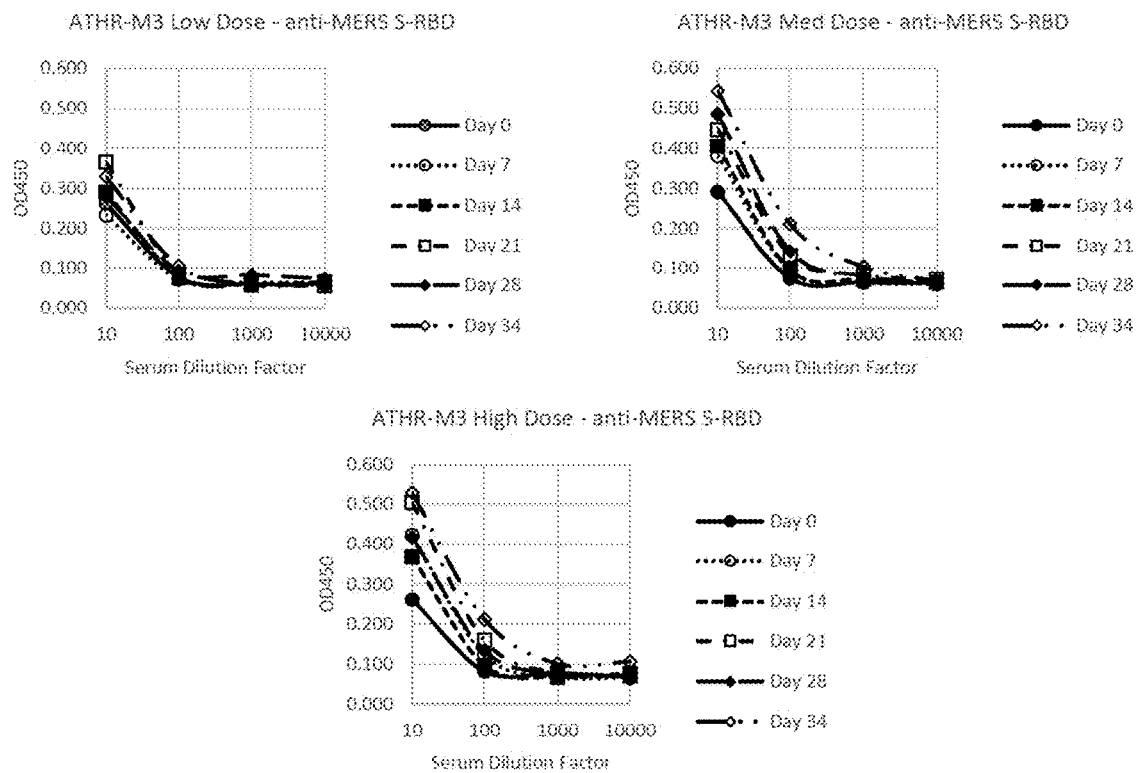
FIG. 23 illustrates serum antibody levels obtained for an antibody against another antigen of a multi-valent vaccine comprising ATHR-M3 as described herein.
Figure 24:
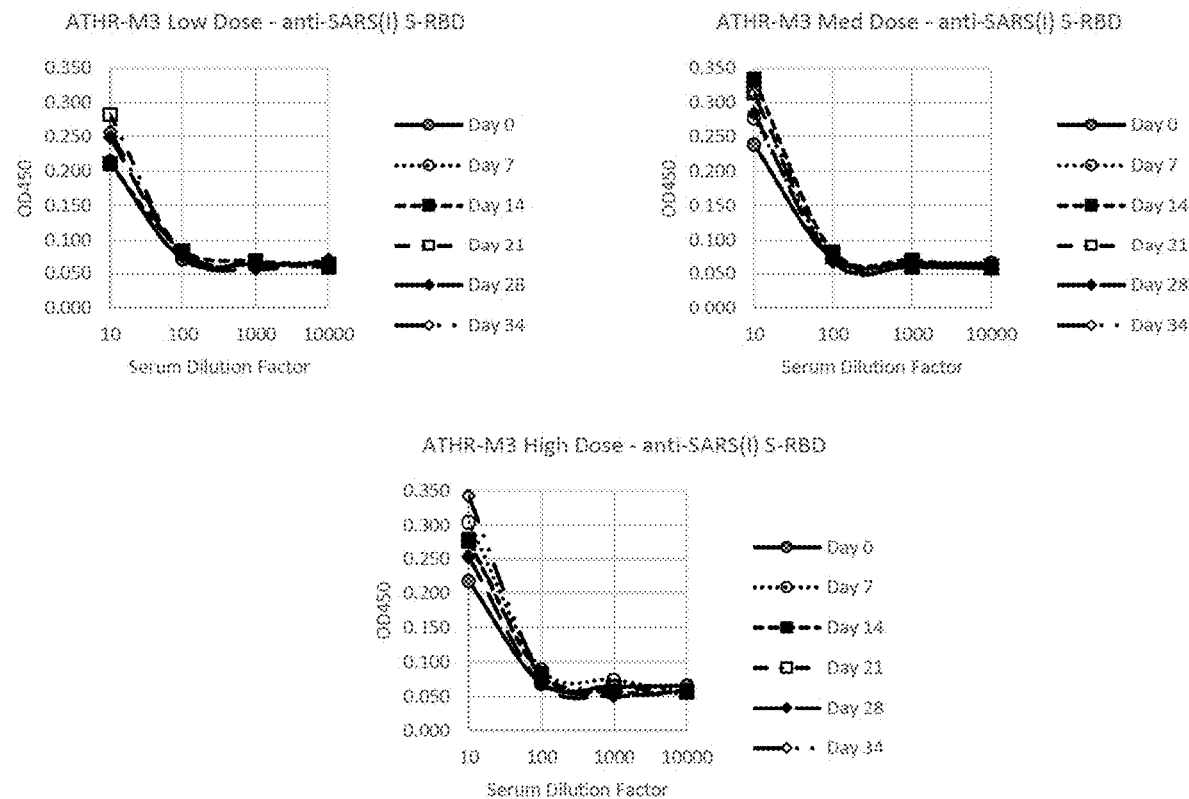
FIG. 24 illustrates serum antibody levels obtained for an antibody against another antigen of a multi-valent vaccine comprising ATHR-M3 as described herein.
Figure 25:
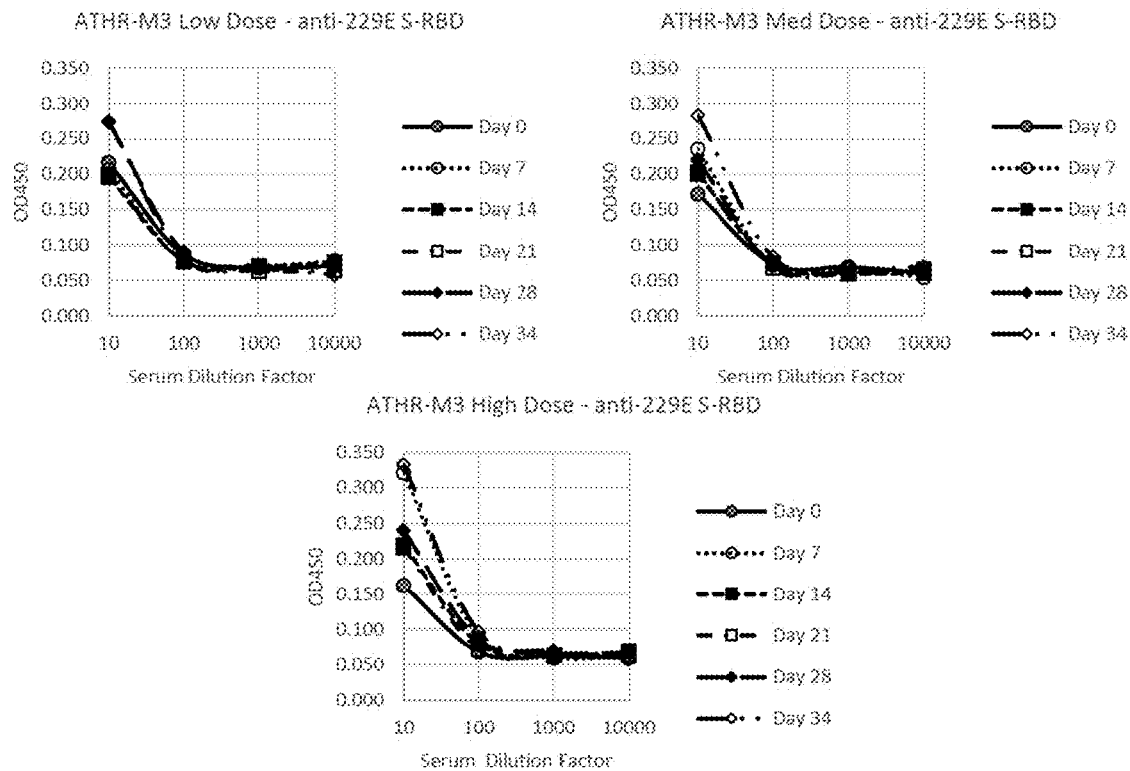
FIG. 25 illustrates serum antibody levels obtained for an antibody against another antigen of a multi-valent vaccine comprising ATHR-M3 as described herein.
Figure 26:
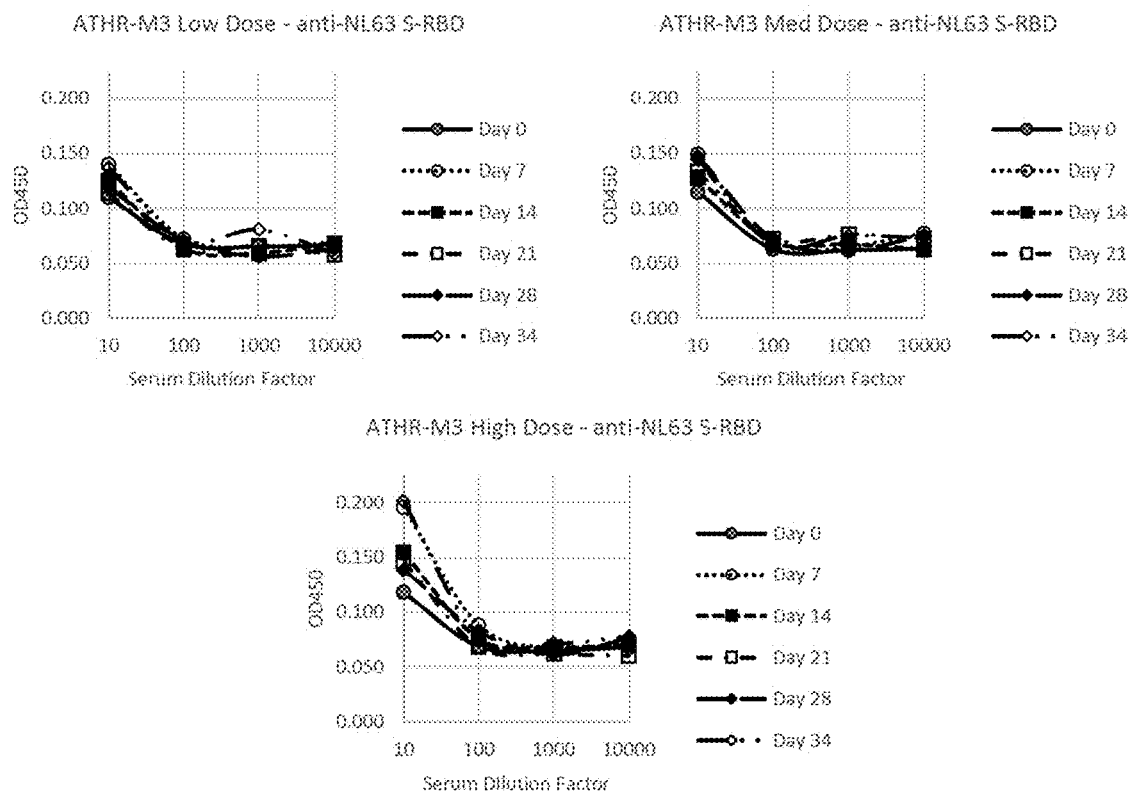
FIG. 26 illustrates serum antibody levels obtained for an antibody against o another antigen of a multi-valent vaccine comprising ATHR-M3 as described herein.

Serum antibody levels from each group of the vaccination study for anti-COVID-19 SRBD are shown in FIG. 22; anti-MERS SRBD data are shown in FIG. 23; anti-SARS(I) SRBD data are shown in FIG. 24; anti-229E SRBD data are shown in FIG. 25; and anti-NL63 SRBD data are shown in FIG. 26. Serum was collected on days 0, 7, 14, 21, 28, and 34. Collected serum was diluted 10-10,000-fold and examination was carried out via ELISA assay, in which recombinant S-RBD from the pathogen of interest was coated and detection was obtained by use of anti-human IgG, IgM, and IgA. The OD450 signal was averaged for n=7 (days 0-21) and n=4 (days 28-34).

Figure 27:
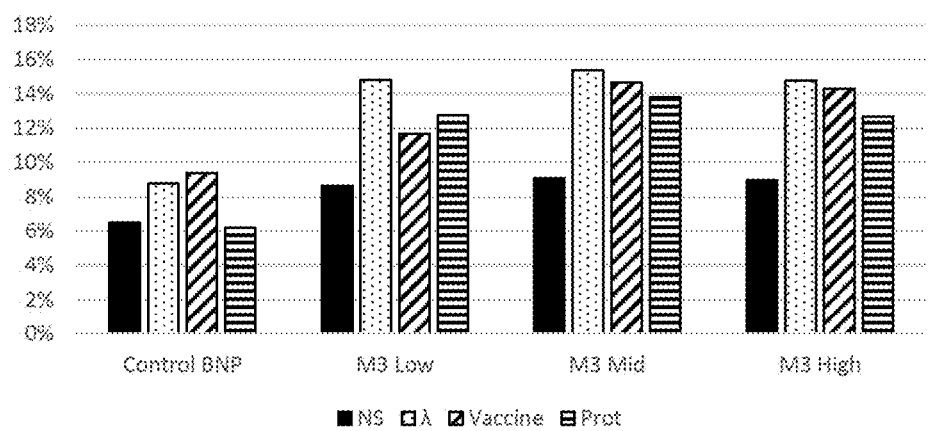
FIG. 27 graphically illustrates the B-cell response of subjects to the multi-valent vaccine comprising ATHR-M3.
Figure 27:
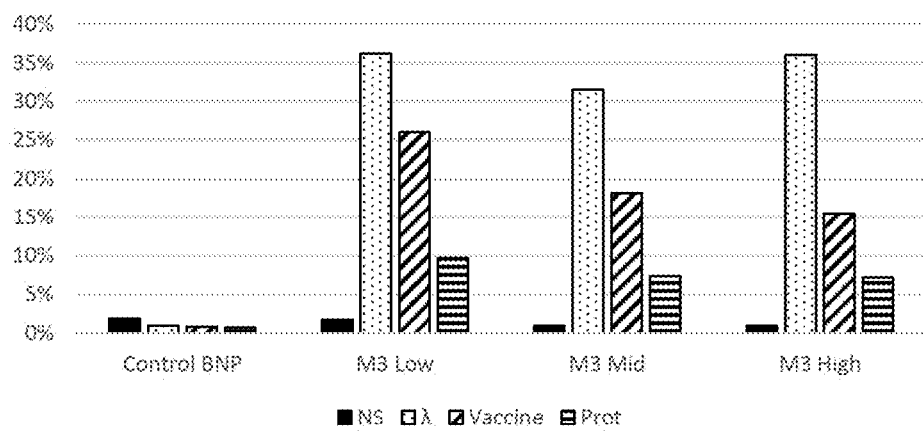
Figure 28:
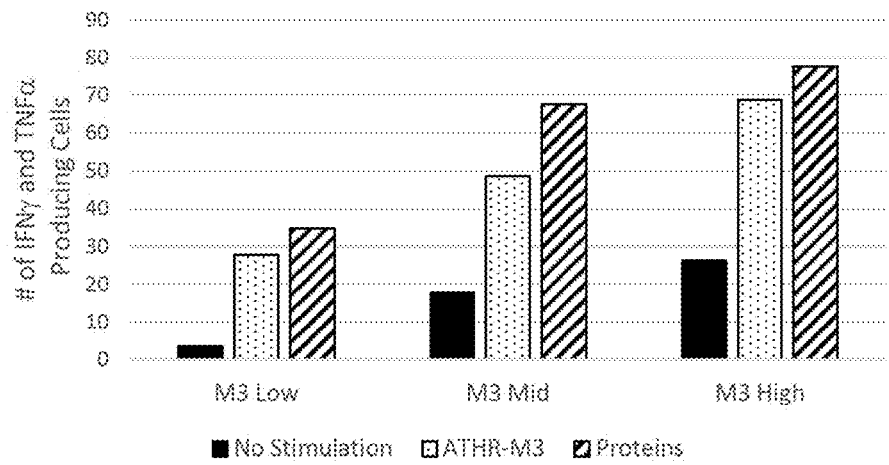
FIG. 28 graphically illustrates the T-cell response of subjects to the multi-valent vaccine comprising ATHR-M3.
Figure 28:
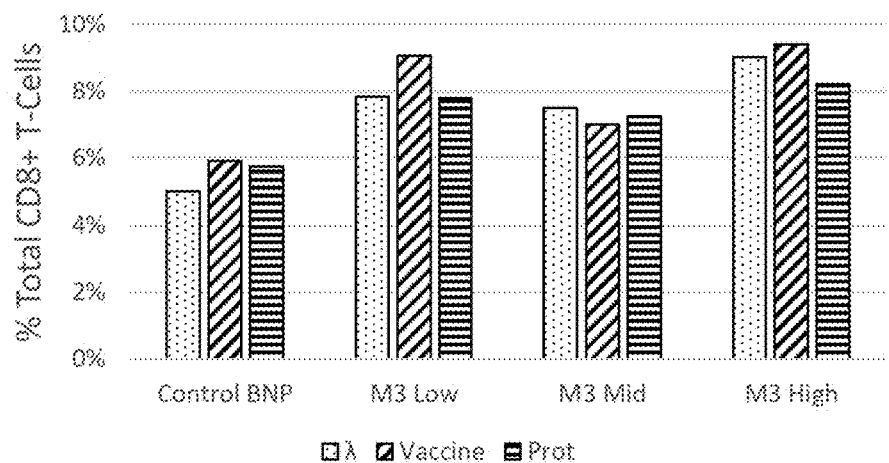
Figure 28:
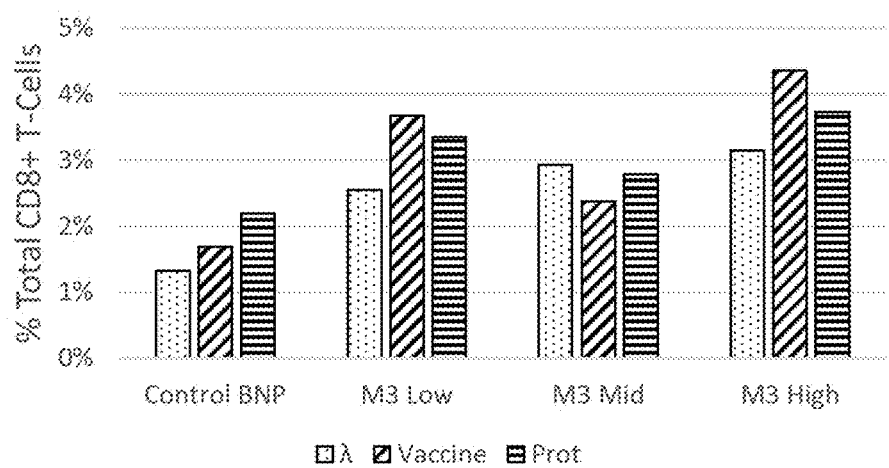

B-cell responses to the vaccine are illustrated in FIG. 27 and T-cell responses are illustrated in FIG. 28. Splenocytes were harvested from vaccinated mice on Day 34 following which in vitro stimulation occurred for 4 days in the presence of one of:

no stimulation
Control bio-nanoparticle (λ phage)
ATHR-M3
recombinant protein (SRBD from COVID, SARS, MERS, 229E, NL63)

The cells were characterized by ELISPOT and/or flow cytometry. As indicated, an increasing number of plasmablasts (B-cell precursors) and plasma cells (mature IgG secreting B-cells) were seen as a function of vaccination with ATHR-M3 (FIG. 27) and both ATHR-3 and recombinant proteins stimulated T-cell activation (FIG. 28). In addition, a higher percentage of both $CD4^+$ and $CD8^+$ T-cells were found in mice vaccinated with ATHR-M3 as compared to the control phage indicating activation of the cellular immune response specific to vaccination with ATHR-M3.

Example 4

A bacteriophage as described in Example 1, which displays the S-RBD of SARS-Cov-2, or in Example 2 which displays the 5 fragment of the spike protein and 2 fragments of the nucleocapsid protein, or in Example 3 which displays the S-RBD domains of multiple strains of coronavirus was engineered to also display a further exogenous polypeptide chain fused to gpD/linker. This further fusion coat protein encodes amino acids 112-261 of CD40L (also known as CD154) (SEQ ID NO: 15).

```
                                                      SEQ ID NO: 15
  1 MTSKETFTHYQPQGNSDPAHTATAPGGLSAKAPAMTPLMLDTSSRKLVAW    50

51 DGTTDGAAVGILAVAADQTSTTLTFYKSGTFRYEDVLWPEAASDETKKRT   100

101 AFAGTAISIVGGSGPVGPGGSGASGDQNPQIAAHVISEASSKTTSVLQWA   150

151 EKGYYTMSNNLVTLENGKQLTVKRQGLYYIYAQVTFCSNREASSQAPFIA   200

201 SLCLKSPGRFERILLRAANTHSSAKPCGQQSIHLGGVFELQPGASVFVNV   250

251 TDPSQVSHGTGFTSFGLLKL                                270
```

The DNA encoding the gpD-linker-CD40L fusion protein (SEQ ID NO: 15) was cloned into the expression vector pCDFDuet-1 (Novagen) in the second multi-cloning site at the restriction site for NdeI for co-expression with the vectors used for expression of ATHR-M1 and ATHR-M3 to yield ATHR-M4 and ATHR-M6 respectively. Alternatively, the DNA encoding the gpD-linker-CD40L fusion protein (SEQ ID NO: 15) was cloned into the expression vector pCOLA-S1c (constructed in Example 2) in the second multi-cloning site at the restriction site for NdeI. This allowed for co-expression with the vectors used for expression on ATHR-M2 to yield ATHR-M5.

Natural CD40L expressed on T-helper cells binds to CD40 on B-cells inducing their conversion to memory B-cells. In a similar fashion, ATHR-M4, ATHR-M5 and ATHR-M6 are expected to engage B-cells both through their B-cell receptors, surface immunoglobulins specific to the targeted antigens, as well as through CD40 on the B-cell and CD40L expressed on the vaccine, inducing the conversion of the B-cell to a memory phenotype. In this way, the engineered bacteriophage can exhibit an immune response with "memory enhancement" and can be delivered as an initial vaccine or may be used to boost subjects after initial vaccination with a vaccine that does not include the memory enhancement component, e.g., that only displays the S-RBD of SARS-CoV-2.

Figure 29:
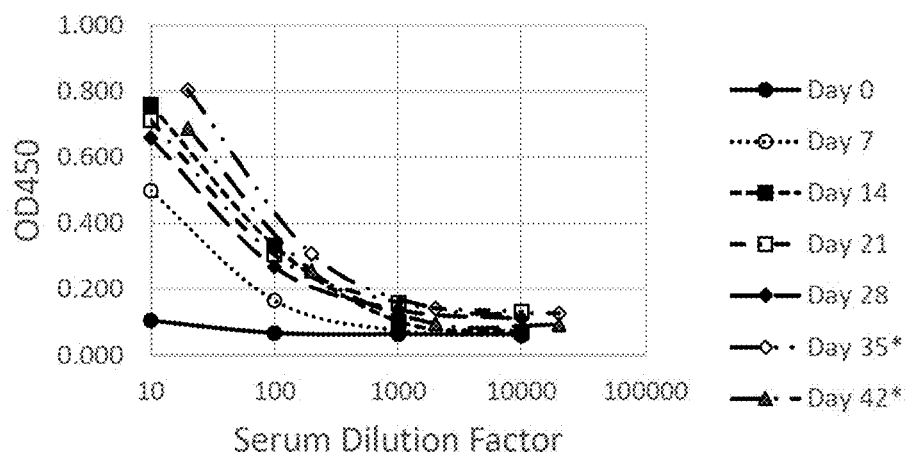
FIG. 29 compares serum antibody levels obtained for subjects immunized with a vaccine comprising ATHR-M1, subjects immunized with a vaccine comprising ATHR-M4, and subjects immunized with a vaccine comprising ATHR-M1 for the initial vaccination followed by ATHR-M4 for a boost.
Figure 29:
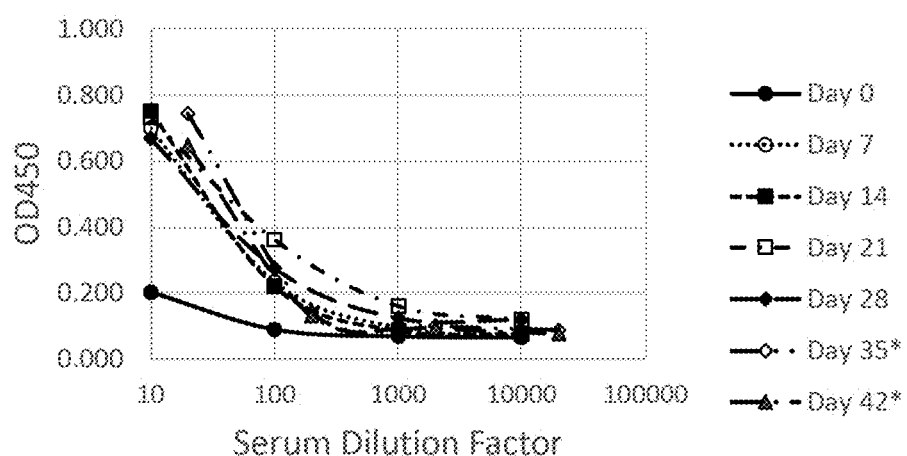
Figure 29:
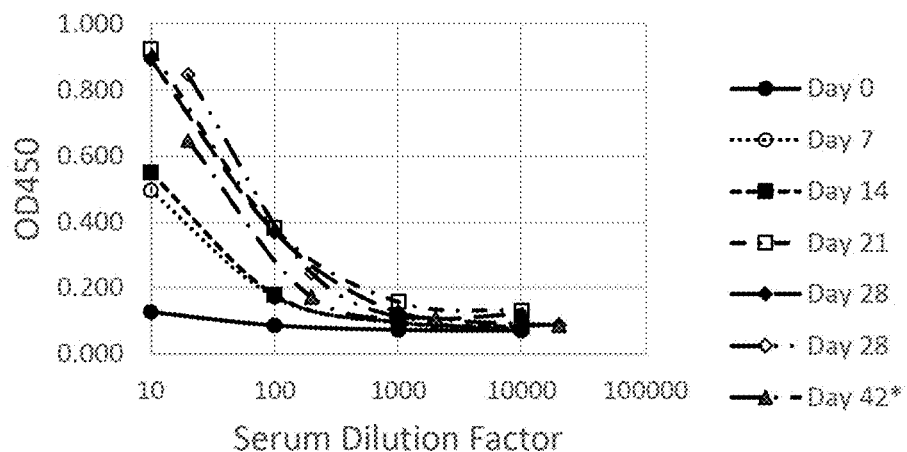

An immunogenicity study was performed directly comparing vaccination and boost of balb/c mice with ATHR-M1, ATHR-M4 or ATHR-M1 for the initial vaccination followed by ATHR-M4 for the boost. Mice were vaccinated on day 1 and boosted on day 14. All doses were $5 \times 10^{10}$ phage and there were seven mice per group with 3 sacrificed on day 7 (only receiving initial vaccination), 3 sacrificed on day 28 and one sacrificed on day 42. Serum was collected from the mice every 7 days as well as on the day of sacrifice. FIG. 29 compares the serum antibody levels against S-RBD in the three groups. While all groups reach high titers of serum antibody, the most rapid response is seen in the group that received the "memory-enhanced" ATHR-M4 at both vaccination and boost, however, the group that received ATHR-M1 at vaccination and ATHR-M4 at boost achieved the highest serum antibody levels.

Figure 30:
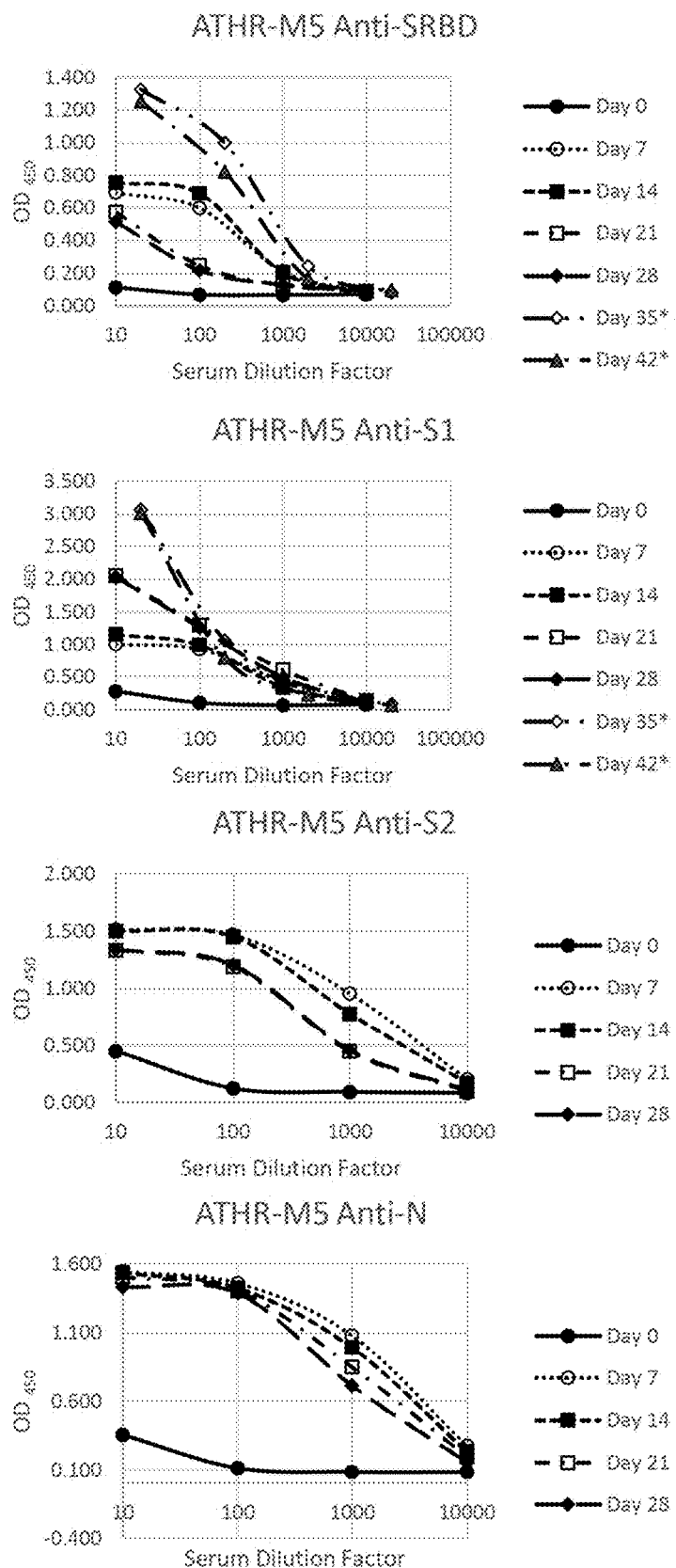
FIG. 30 compares serum antibody levels obtained for subjects immunized with a vaccine comprising ATHR-M2, subjects immunized with a vaccine comprising ATHR-M5, and subjects immunized with a vaccine comprising ATHR-M2 for the initial vaccination followed by ATHR-M5 for a boost.

An immunogenicity study was performed directly comparing vaccination and boost of balb/c mice with ATHR-M2, ATHR-M5 or ATHR-M2 for the initial vaccination followed by ATHR-M5 for the boost. Mice were vaccinated on day 1 and boosted on day 14. All doses were $5 \times 10^{10}$ phage and there were seven mice per group with 3 sacrificed on day 7 (only receiving initial vaccination), 3 sacrificed on day 28 and one sacrificed on day 42. Serum was collected from the mice every 7 days as well as on the day of sacrifice. While all groups reach high titers of serum antibody, the most rapid and robust responses were seen in the group that received the "memory-enhanced" ATHR-M5 at both vaccination and boost. FIG. 30 presents the serum antibody titers against S-RBD, S1, S2 and N in for the animals that received ATHR-M5 at both vaccination and boost.

A similar immunogenicity study was performed comparing vaccination and boost of balb/c mice with ATHR-M3, ATHR-M6 or ATHR-M3 for the initial vaccination followed by ATHR-M6 for the boost. Similar results were noted indicating more rapid and robust immune responses in the group receiving ATHR-M6.

Example 5

In this example, protein fragments from multiple viral variants of a single viral strain were displayed on the same multivalent phage. Specifically, the display of the S1 and S2 domains of several variants of the spike protein from SARS-CoV-2 were presented on the same phage using the process outlined in Example 1. Exogenous peptide sequences of the phage included the following:

SARS-CoV-2 S1 (amino acid residues 16-690) as a fusion protein with gpD/linker was cloned into pETDuet-1 (Novagen) at the NcoI site, while SARS-CoV-2 S2 (amino acid residues 691-1213) as a fusion protein with gpD/linker was cloned into the NdeI site of the same vector.

Variant B.1.1.1.7 S1 (amino acid residues 16-690) as a fusion protein with gpD/linker was cloned into pACYC-Duet-1 (Novagen) at the NcoI site, while B.1.1.1.7 S2 (amino acid residues 691-1213) as a fusion protein with gpD/linker was cloned into the NdeI site of the same vector.

Variant B.1.135 S1 (amino acid residues 16-690) as a fusion protein with gpD/linker was cloned into pCDFDuet-1 (Novagen) at the NcoI site. The second site in this vector is used for the expression of the CD40L fusion protein as described in Example 4.

Variant P.1 S1 (amino acid residues 16-690) as a fusion protein with gpD/linker was cloned into pCOLADuet-1 (Novagen) at the NcoI site, while P.1 S2 (amino acid residues 691-1213) as a fusion protein with gpD/linker was cloned into the NdeI site of the same vector.

All four expression vectors were co-transfected into *E. coli* LE392 and the *E. coli* were selected on chloramphenicol, kanamycin, ampicillin and streptomycin containing medium. Phage expression, isolation, endotoxin removal and characterization were as above in Example 1 except that the parent lambda phage strain used was CE6 (Novagen). These phage were designated as ATHR-M7 (without the CD40L) and ATHR-M8 (with display of CD40L).

While certain embodiments of the disclosed subject matter have been described using specific terms, such description is for illustrative purposes only, and it is to be understood that changes and variations may be made without departing from the spirit or scope of the subject matter.

What is claimed is:

1. An engineered bacteriophage comprising:
   a first fusion coat protein comprising a first exogenous polypeptide directly or indirectly fused to a first coat protein of a bacteriophage; and
   a second fusion coat protein comprising a second exogenous polypeptide directly or indirectly fused to a second coat protein of the bacteriophage; wherein
   the engineered bacteriophage includes a capsid head that encloses a DNA or RNA genome, and wherein
   the engineered bacteriophage is free of nucleic acid sequences encoding the first exogenous polypeptide and the second exogenous polypeptide; and wherein
   the first exogenous polypeptide differs from the second exogenous polypeptide and/or the first coat protein differs from the second coat protein.

2. The engineered bacteriophage of claim 1, wherein the first coat protein and the second coat protein are independently selected from the group consisting of gpD, gpE, gpC, pVIII, pIII, pVI, pVII, pIX, gp23, gp24, gp10A, gp10B, gpF, and gpG coat proteins.

3. The engineered bacteriophage of claim 1, wherein the first exogenous polypeptide and the second exogenous polypeptide are the same as one another or are developed from the same protein, or are variants of one another.

4. The engineered bacteriophage of claim 1, wherein the first exogenous polypeptide and the second exogenous polypeptide are developed from different proteins and are from a single source or are from different sources.

5. The engineered bacteriophage of claim 1, further comprising one or more additional exogenous polypeptides, the one or more additional exogenous polypeptides being directly or indirectly fused to one or more additional coat proteins of the bacteriophage as one or more additional fusion coat proteins or the one or more additional exogenous polypeptides being directly or indirectly fused to the first coat protein or the second coat protein.

6. A method for forming the engineered bacteriophage of claim 1, the method comprising:
   transfecting a bacterial cell with one or more expression plasmids, the one or more expression plasmids including a first nucleic acid sequence that encodes the first fusion coat protein and a second nucleic acid sequence that encodes the second fusion coat protein, the one or more expression plasmids comprising regulatory sequences such that the first and second fusion coat proteins are transiently expressed by the bacterial cell following the transfection; and
   infecting the bacterial cell with a bacteriophage; wherein upon the transfection and the infection, the engineered bacteriophage is produced by the bacterial cell, the engineered bacteriophage including the first fusion coat protein and the second fusion coat protein with the first and second exogenous polypeptides at a surface of the bacteriophage.

7. The method of claim 6, wherein the one or more expression plasmids include a single expression plasmid that includes the first nucleic acid sequence and the second nucleic acid sequence, and/or wherein the one or more expression plasmids includes a first expression plasmid that includes the first nucleic acid sequence and a second expression plasmid that includes the second nucleic acid.

8. The method of claim 6, wherein the regulator sequences comprise a first promoter driving expression of the first fusion coat protein and a second promoter driving expression of the second fusion coat protein, wherein the first promoter and the second promoter are the same promoter or are different promoters.

9. The method of claim 8, wherein the first promoter and the second promoter are different promoters having different strengths from one another and/or wherein the first promoter and the second promoter are independently selected from an inducible promoter and a native phage promoter.

10. The method of claim 6, wherein the bacteriophage that infects the bacterial cell has been modified such that expression of the wild type first coat protein and/or the wild type second coat protein has been silenced.

11. A vaccine comprising an immunogenic engineered bacteriophage, the immunogenic engineered bacteriophage including a first fusion coat protein, the first fusion coat protein including a first exogenous polypeptide directly or indirectly fused to a first bacteriophage coat protein, the first exogenous polypeptide comprising a sequence that corresponds to or is derived from a first immunogenic protein of a first pathogen, wherein the immunogenic engineered bacteriophage includes a capsid head that encloses a DNA or RNA genome, and wherein the immunogenic engineered bacteriophage is free of a nucleic acid sequence encoding the first exogenous peptide.

12. The vaccine of claim 11, the immunogenic engineered bacteriophage comprising a second fusion coat protein, the second fusion coat protein including a second exogenous polypeptide directly or indirectly fused to a second bacteriophage coat protein, wherein the first exogenous polypeptide differs from the second exogenous polypeptide and/or the first coat protein differs from the second coat protein.

13. The vaccine of claim 12, wherein the second exogenous polypeptide comprises a sequence that corresponds to or is derived from a second immunogenic protein or is involved in the development of an immune response memory.

14. The vaccine of claim 13, wherein the first immunogenic protein and the second immunogenic protein are both derived from the first pathogen or are derived from first and second different pathogens.

15. The vaccine of claim 11, wherein the first pathogen comprises a bacterium, a fungus, a parasite, or a virus.

16. The vaccine of claim 14, wherein the first pathogen comprises a coronavirus selected from the group consisting of SARS-CoV-1, SARS-Cov-2, MERS, HKU1, NL63, OC43 and 229E, influenza, HIV, HCV, HBV, HPV, dengue, Chikungunya, or a West Nile virus.

17. The vaccine of claim 11, wherein the first immunogenic protein comprises a Spike protein, a Nucleocapsid protein, a Membrane protein, or an Envelope protein, or wherein the first exogenous polypeptide comprises a sequence that corresponds to or is derived from a receptor binding domain of a Spike protein.

18. A vaccination protocol comprising administering a vaccine as in claim 11 to an individual, the vaccination protocol further optionally comprising administration of one or more booster vaccinations, wherein the protocol is a prophylactic protocol or a therapeutic protocol.

19. A method of forming the vaccine of claim 11 comprising:
transfecting a bacterial cell with a first expression plasmid, the first expression plasmid including a first nucleic acid sequence that encodes the first fusion coat protein, the first expression plasmid comprising regulatory sequences such that the first fusion coat protein is transiently expressed by the bacterial cell following the transfection; and
infecting the bacterial cell with a bacteriophage; wherein upon the transfection and the infection, the immunogenic engineered bacteriophage is produced by the bacterial cell.

20. The method of claim 19, wherein the first expression plasmid further comprises a second nucleic acid sequence that encodes a second fusion coat protein, the second fusion coat protein including a second exogenous polypeptide directly or indirectly fused to a second coat protein, wherein the first exogenous polypeptide differs from the second exogenous polypeptide and/or the first coat protein differs from the second coat protein.

21. The method of claim 19, further comprising transfecting the bacterial cell with a second expression plasmid, the second expression plasmid comprising a second nucleic acid sequence that encodes a second fusion coat protein, the second fusion coat protein including a second exogenous polypeptide directly or indirectly fused to a second coat protein, wherein the first exogenous polypeptide differs from the second exogenous polypeptide and/or the first coat protein differs from the second coat protein.

\* \* \* \* \*